United States Patent
Steier et al.

(10) Patent No.: US 11,733,506 B2
(45) Date of Patent: *Aug. 22, 2023

(54) USER WEARABLE FLUORESCENCE ENABLED VISUALIZATION SYSTEM

(71) Applicant: Designs for Vision, Inc., Bohemia, NY (US)

(72) Inventors: Liviu Steier, Needham, MA (US); Richard E. Feinbloom, New York, NY (US)

(73) Assignee: Designs for Vision, Inc., Bohemia, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/722,833

(22) Filed: Apr. 18, 2022

(65) Prior Publication Data

US 2022/0244524 A1 Aug. 4, 2022

Related U.S. Application Data

(60) Continuation of application No. 17/357,909, filed on Jun. 24, 2021, now Pat. No. 11,307,402, which is a
(Continued)

(51) Int. Cl.
*G02B 25/02* (2006.01)
*F21V 21/084* (2006.01)
(Continued)

(52) U.S. Cl.
CPC ............ *G02B 25/02* (2013.01); *A61B 5/0017* (2013.01); *A61B 5/0077* (2013.01); *A61B 5/7225* (2013.01); *A61B 90/30* (2016.02); *A61B 90/35* (2016.02); *A61B 90/50* (2016.02); *F21V 5/008* (2013.01); *F21V 5/04* (2013.01); *F21V 7/041* (2013.01); *F21V 11/08* (2013.01);
(Continued)

(58) Field of Classification Search
None
See application file for complete search history.

(56) References Cited

U.S. PATENT DOCUMENTS 2,986,969 A 6/1961 Muncheryan
3,273,456 A 9/1966 Feinbloom
(Continued)

OTHER PUBLICATIONS

"A Multi-Detection Fluorescence Dye with 5-ALA and ICG Using Modified Light Emitting Diodes," Yoon, K, et. al, Current Optics and Photonics, vol. 3, No. 3, Jun. 2019, pp. 256-262.
(Continued)

*Primary Examiner* — Ashok Patel
(74) *Attorney, Agent, or Firm* — Law Office of Carl Giordano, PC

(57) ABSTRACT

A user-wearable fluorescence based visualization system comprising a multi-light lamp assembly that provides for the selected output of light using multiple light emitting sources, wherein the outputted light may be tailored to generate response wavelength by the interaction of the emitted light and a tissue illuminated by the emitted light, through the process of fluorescence, and a viewing system that allows a practitioner view the fluorescent light generated by the tissue, and distinguish between healthy and diseased tissues.

21 Claims, 21 Drawing Sheets

Related U.S. Application Data division of application No. 17/134,309, filed on Dec. 26, 2020, now Pat. No. 11,099,376.

(60) Provisional application No. 63/013,487, filed on Apr. 21, 2020.

(51) Int. Cl.
| | |
|---|---|
| *F21V 23/04* | (2006.01) |
| *G02B 25/00* | (2006.01) |
| *G02B 5/20* | (2006.01) |
| *A61B 90/30* | (2016.01) |
| *A61B 5/00* | (2006.01) |
| *A61B 90/35* | (2016.01) |
| *A61B 90/50* | (2016.01) |
| *F21V 5/00* | (2018.01) |
| *F21V 5/04* | (2006.01) |
| *F21V 7/04* | (2006.01) |
| *F21V 11/08* | (2006.01) |
| *F21V 19/02* | (2006.01) |
| *F21V 23/00* | (2015.01) |
| *F21V 14/02* | (2006.01) |
| *G02C 7/08* | (2006.01) |
| *F21Y 113/10* | (2016.01) |
| *F21Y 115/10* | (2016.01) |

(52) U.S. Cl.
CPC .............. *F21V 14/02* (2013.01); *F21V 19/02* (2013.01); *F21V 21/084* (2013.01); *F21V 23/003* (2013.01); *F21V 23/04* (2013.01); *G02B 5/208* (2013.01); *G02B 25/004* (2013.01); *G02B 25/008* (2013.01); *A61B 5/0071* (2013.01); *A61B 5/0088* (2013.01); *A61B 2090/309* (2016.02); *A61B 2090/502* (2016.02); *A61B 2560/0214* (2013.01); *F21Y 2113/10* (2016.08); *F21Y 2115/10* (2016.08); *G02C 7/086* (2013.01)

(56) References Cited

U.S. PATENT DOCUMENTS

| | | | |
|---|---|---|---|
| 3,519,339 | A | 7/1970 | Hutchinson |
| 4,089,117 | A | 5/1978 | Villarreal |
| 4,511,225 | A | 4/1985 | Lipson |
| 5,162,647 | A | 11/1992 | Field, Jr. |
| 5,751,340 | A | 5/1998 | Strobl |
| 6,212,425 | B1 | 4/2001 | Irion |
| 7,008,074 | B1 | 3/2006 | Halm |
| 7,477,451 | B2 | 1/2009 | Katz |
| 7,532,394 | B2 | 5/2009 | Gebelein |
| 8,120,847 | B2 | 2/2012 | Chang |
| 8,215,791 | B2 | 7/2012 | Feinbloom |
| 9,791,138 | B1 | 10/2017 | Feinbloom |
| 10,054,775 | B2 | 8/2018 | Haugen |
| 10,061,115 | B2 | 8/2018 | Feinbloom |
| 10,132,483 | B1 | 11/2018 | Feinbloom |
| 10,215,977 | B1 | 2/2019 | Feinbloom |
| 10,240,769 | B1 | 3/2019 | Braganca |
| 10,437,041 | B1 | 10/2019 | Feinbloom |
| 10,896,573 | B2 | 1/2021 | Feinbloom |
| 11,109,762 | B1 * | 9/2021 | Steier .................... G02C 11/04 |
| 2001/0005281 | A1 | 6/2001 | Yu |
| 2002/0067560 | A1 | 6/2002 | Jones |
| 2002/0097230 | A1 | 7/2002 | Lowry |
| 2003/0002036 | A1 | 1/2003 | Haan |
| 2007/0047073 | A1 | 3/2007 | Zimmer |
| 2008/0017787 | A1 | 1/2008 | Okawa |
| 2008/0219654 | A1 | 9/2008 | Border |
| 2009/0073558 | A1 | 3/2009 | Jacobs |
| 2010/0053540 | A1 | 3/2010 | Blayden |
| 2010/0210951 | A1 | 8/2010 | Rahman |
| 2010/0305436 | A1 | 12/2010 | Chen |
| 2011/0270035 | A1 | 11/2011 | Gono |
| 2012/0120636 | A1 | 5/2012 | Wilt |
| 2014/0036356 | A1 | 2/2014 | Feinbloom |
| 2014/0210972 | A1 | 7/2014 | On |
| 2015/0253589 | A1 | 9/2015 | Finkman |
| 2021/0338082 | A1 * | 11/2021 | Steier .................... F21V 17/002 |

OTHER PUBLICATIONS

European Search Report—dated Feb. 14, 2022.
European Search Report—dated Jul. 5, 2021.

* cited by examiner

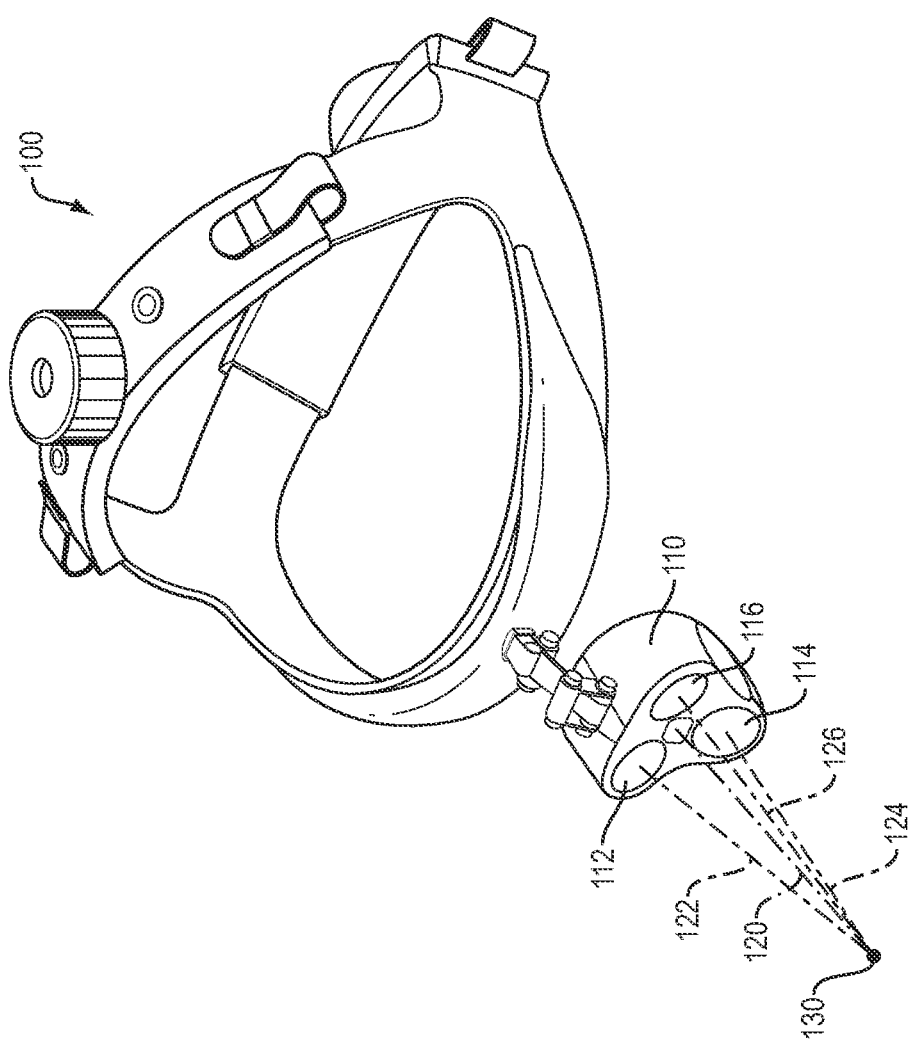

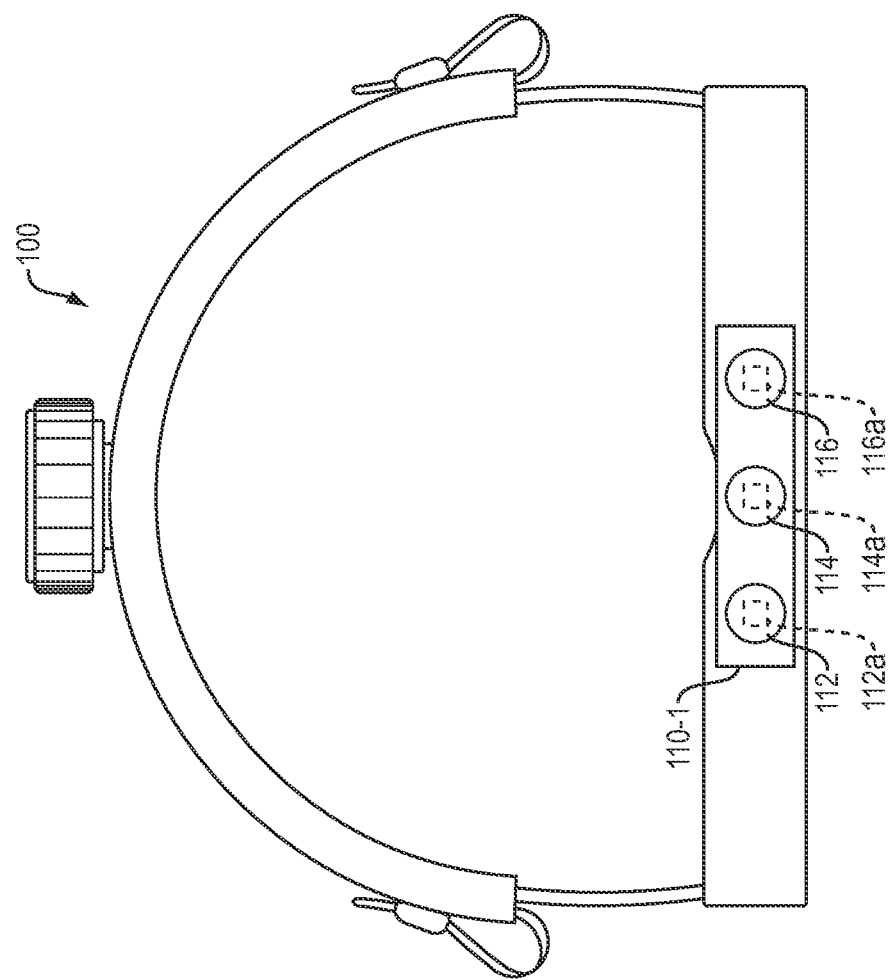

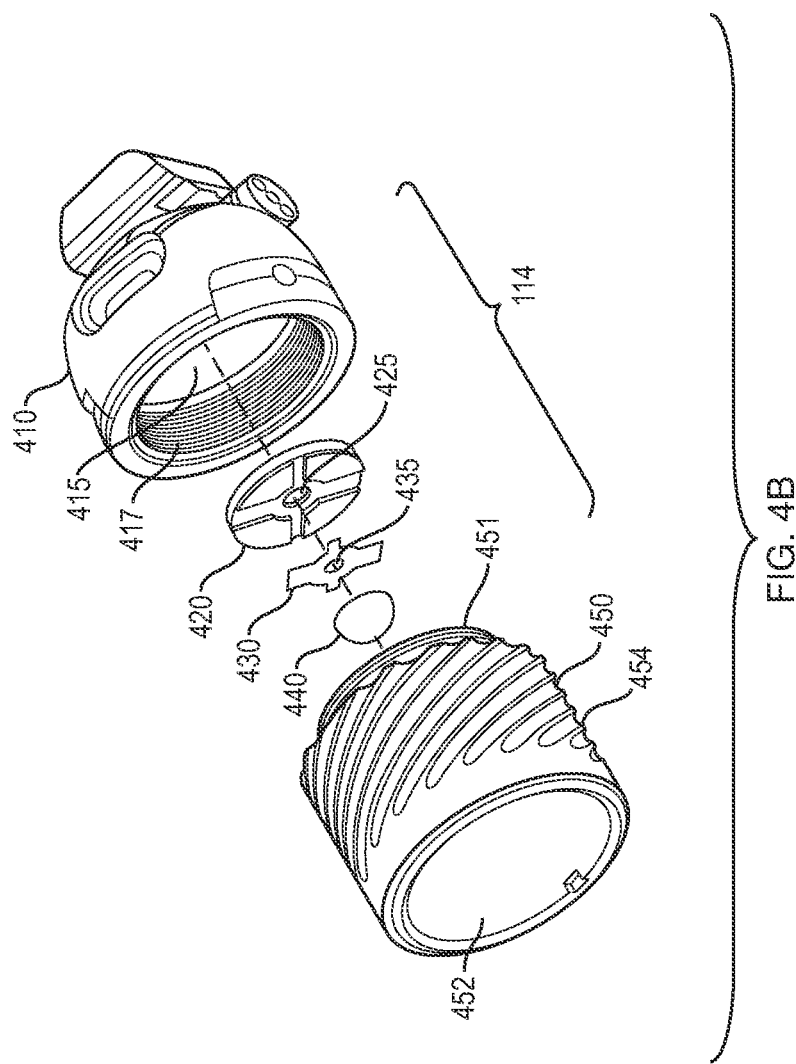

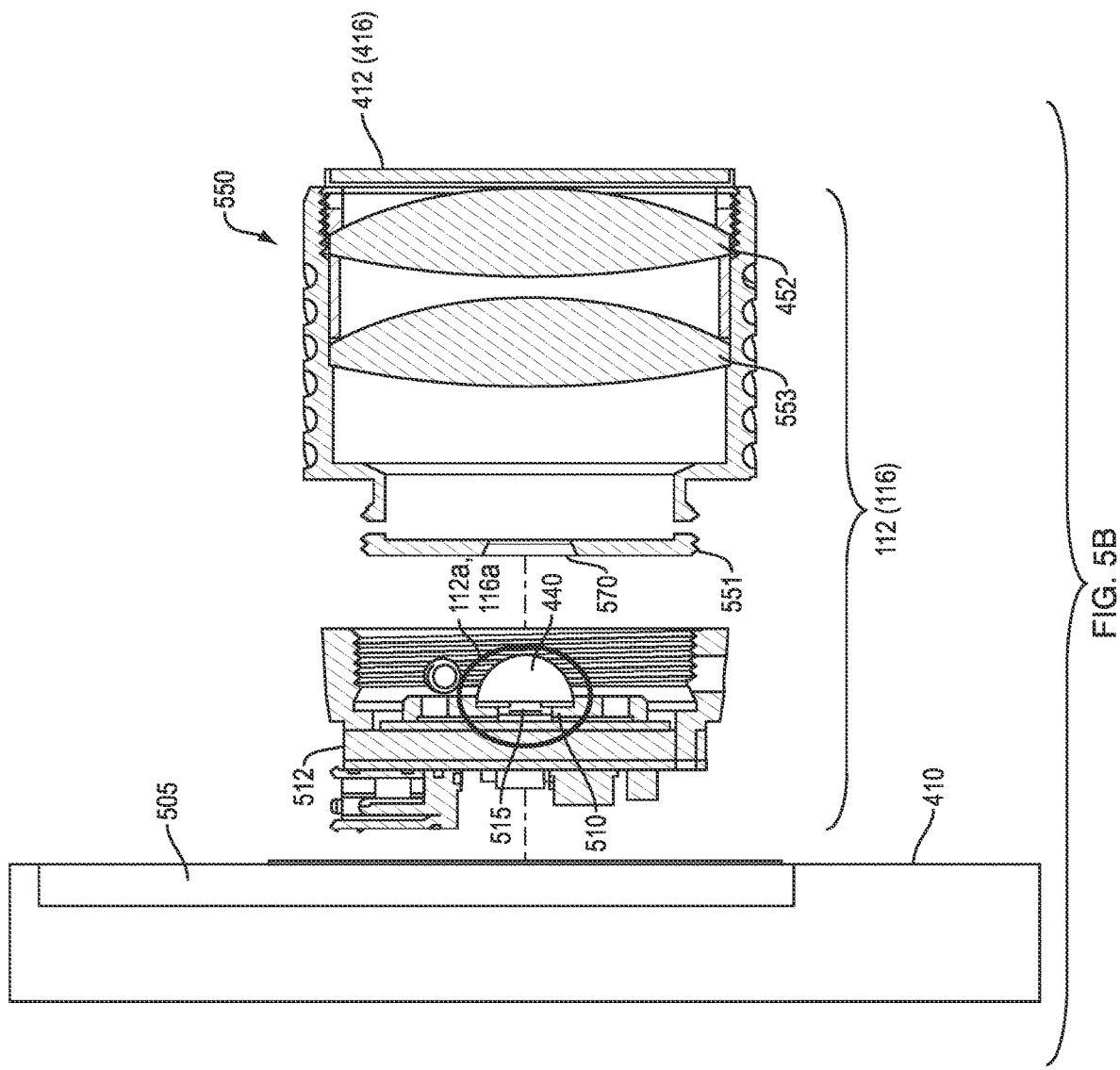

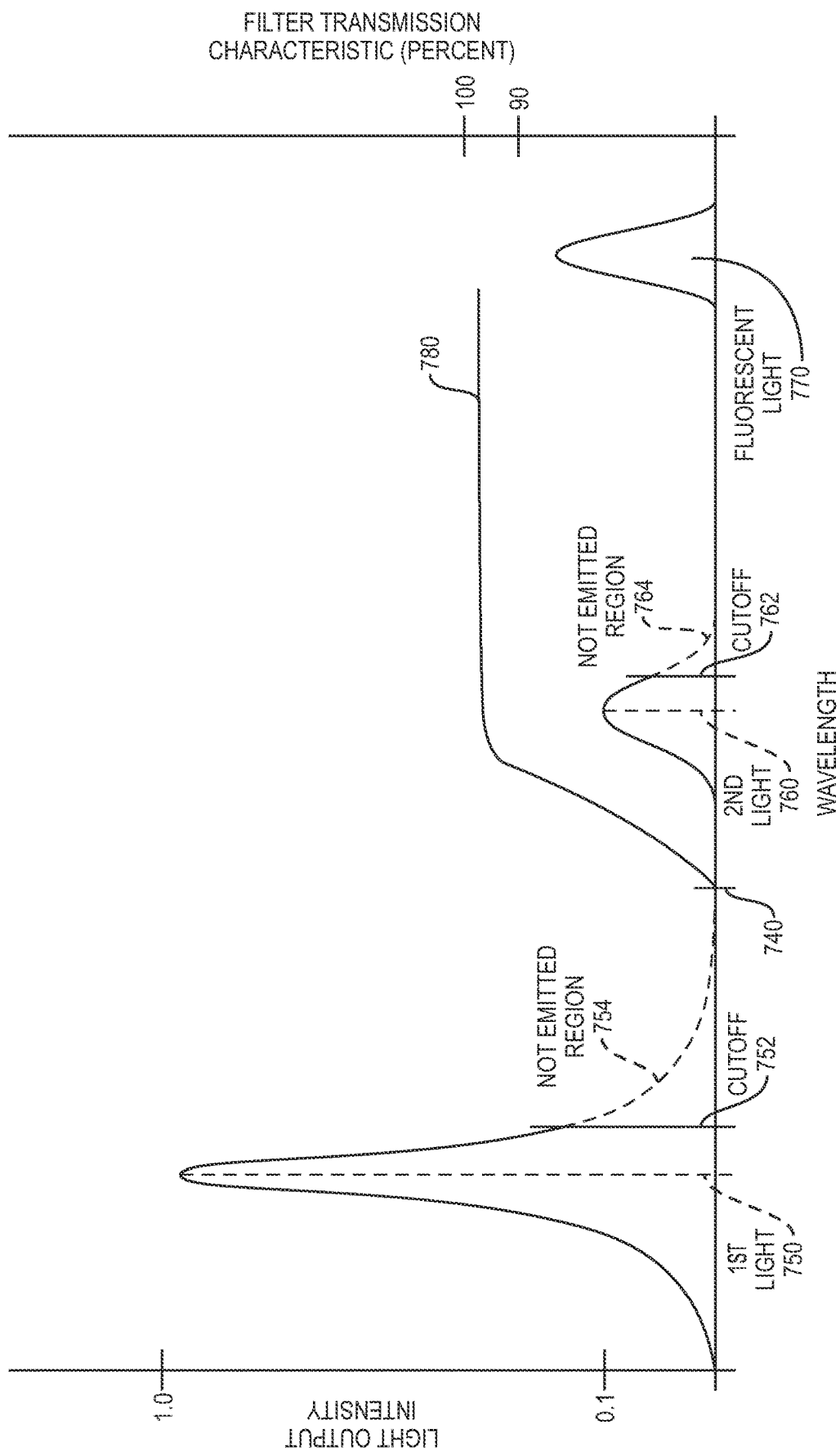

USER WEARABLE FLUORESCENCE ENABLED VISUALIZATION SYSTEM

CLAIM OF PRIORITY

This application claims, pursuant to 35 USC 120, as a Continuation application, priority to, and the benefit of the earlier filing date of patent application Ser. No. 17/357,909, filed on Jun. 24, 2021, which claimed, pursuant to 35 USC 120, as a Divisional application, priority to, and the benefit of the earlier filing date, of patent application Ser. No. 17/134,309, filed on Dec. 26, 2020, which claimed, pursuant to 35 USC 119, as a non-provisional application of that patent application filed on Apr. 21, 2020 and afforded Ser. No. 63/013,487, the contents of all of which are incorporated by reference, herein.

RELATED APPLICATIONS

This application is related to the teaching of U.S. Pat. Nos. 7,690,806; 8,215,791; RE46463, 9,791,138; 10,061,115; 10,132,483; 10,215,977; 10,240,769; 10,247,384 and 10,437,041, which are assigned to the Assignee of the instant application, and whose contents are incorporated by reference, herein.

This application is further related to filed application Ser. No. 17/134,311 and Ser. No. 17/134,312, whose contents are incorporated by reference, herein.

BACKGROUND OF THE INVENTION

Field of the Invention

The invention is related to optical devices, and more particularly, to optical devices for use in medical and/or dental operations.

Background Information

Light Emitting Diodes (LEDs), whether lasing or non-lasing, (referred to herein as LED) have found utility in the fields of surgery, medicine, and dentistry to provide illumination on the work area of the doctor, surgeon, or dentist. Specialized lighting devices have also found use in distinguishing healthy tissue from diseased tissue. For example, in the field of dental procedures, fluorescence-based methods are often used to provide an objective assessment of a carious process.

Fluorescence is a form of photoluminescence, which through the absorption of light by an object, or by a tissue, etc., causes the generation and spontaneous emission of light of a different wavelength.

In surgery and dentistry, fluorescence is known to be used to distinguish tumors from healthy cells to afford doctors and surgeons guidance during operations to assist in the removal of tumors.

However, the devices created to assist the practitioner in the use of fluorescence in dental and medical procedures are both expensive and cumbersome to use during medical and/or dental procedures. See for example, the KINWVO 900 Robotic Visualization System with the required Blue400 Adapter by Carl Zeiss Meditec AG, Jena, Germany.

Accordingly, there is a need in the industry for portable, user-wearable, devices that provide for the illumination of tissues or objects and the subsequent visualization of differences in the tissue samples or objects using fluorescence technology during medical and/or dental procedures.

SUMMARY OF THE INVENTION

In one aspect of the invention, a light-weight portable device for the viewing and distinguishing of healthy tissue from diseased tissue is disclosed.

In one aspect of the invention, a user wear-able device provides for the viewing and distinguishing of healthy tissue from diseased tissue is disclosed.

In one aspect of the invention, a controlling mechanism for controlling the light output suitable for distinguishing healthy tissue from diseased tissue is disclosed.

In one aspect of the invention, a user wear-able device suitable for use in the dental arts to distinguish healthy tissue in a patient's mouth from diseased tissue, such as cavities is disclosed.

In one aspect of the invention, a user wear-able device suitable for use in the medical arts, such as surgery, to distinguish healthy tissue from diseased tissue is disclosed.

In accordance with the principles of the invention, a multi-light lamp assembly is disclosed that provides for the selected output of light using multiple light emitting sources, wherein the outputted light may be tailored to generate an expected response wavelength that allows a practitioner to distinguish between healthy and diseased tissues. Further disclosed is a viewing device, such as an eyewear, that includes a plurality of filters, which are formulated to selectively prevent the ability to view the light transmitted by the light assembly while allowing a desired wavelength of light to be viewed.

BRIEF DESCRIPTION OF THE DRAWINGS

The advantages, nature, and various additional features of the invention will appear more fully upon consideration of the illustrative embodiments described in detail in connection with the accompanying drawings, where like or similar reference numerals are used to identify like or similar elements throughout the drawings:

FIG. 1 illustrates a perspective view of a first exemplary embodiment of a light assembly suitable for use in a visualization system in accordance with the principles of the invention.

FIG. 2B illustrates a frontal view of a second exemplary embodiment of a light assembly suitable for use in a visualization system in accordance with the principles of the invention.

FIG. 4B illustrates an exploded perspective view of a first exemplary lighting element in accordance with the principles of the invention.

FIG. 5B illustrates a cross-sectional view of the second exemplary embodiment of the lighting element shown in FIG. 4B in accordance with the principles of the invention.

FIG. 7C illustrates a graph of an exemplary light emission and filtering capability of a visualization system, in accordance with the principles of the invention.

Figure 2A:
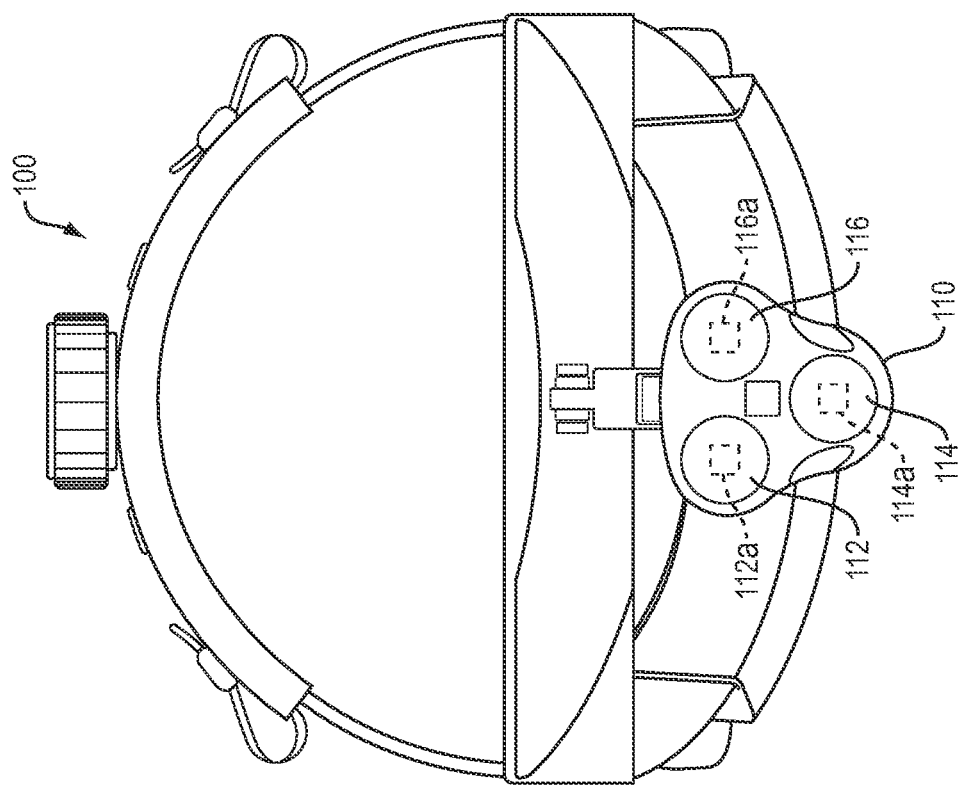
FIG. 2A illustrates a frontal view of the first exemplary embodiment of the light assembly shown in FIG. 1.

It is to be understood that the figures, which are not drawn to scale, and descriptions of the present invention described herein have been simplified to illustrate the elements that are relevant for a clear understanding of the present invention, while eliminating, for purposes of clarity, many other elements. However, because these omitted elements are well-known in the art, and because they do not facilitate a better understanding of the present invention, a discussion of such elements are not provided herein. The disclosure, herein, is directed also to variations and modifications known to those skilled in the art.

DETAILED DESCRIPTION OF THE INVENTION

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "of" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description, herein, should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instances, the terms "about" may include numbers that are rounded (or lowered) to the nearest significant figure.

FIG. 1 illustrates a perspective view of a first exemplary embodiment of a light assembly in accordance with the principles of the invention In this first exemplary embodiment of a light assembly, light assembly 110 is shown suspended from a head band or head strap 100, wherein light assembly 110 includes a plurality of lighting elements 112, 114, 116, concentrically positioned about central (or center) axis 120 extending substantially perpendicular to a plane of light assembly 110. Lighting elements 112, 114, 116 are further illustrated as being oriented at an angle with respect to central axis 120, wherein an angle of orientation of each of lighting elements 112, 114, 116 is such that the light emitted along an optical axis, represented as dashed lines 122, 124 and 126, of corresponding ones of lighting elements 112, 114, 116, respectively, converge on a same point 130 (i.e., a viewing point) along central axis 120 at a known distance from light assembly 110.

Lighting elements 112, 114, 116 may be configured to output a corresponding light independently of each other or in combination with one or more of the other lighting elements 112, 114, 116. The light outputted from lighting elements 112, 114, 116, may, thus, be mixed together at the point of convergence 130 along central axis 120. Or may be individually outputted such that light from one lighting element is presented at point of convergence 130.

The light outputted by lighting elements 112, 114, 116 may, for example, be one of a white light, a near field ultra-violet light, or a visible light in one or more visible light color bands. For example, lighting elements 112, 114, 116 may emit light in an ultra-violet wavelength range of about 10 to about 400 nanometers (nm). Or may emit light in one or more of a visible color light range. For example, in one or more specific color wavelength ranges (e.g., violet—380-435 nm; blue—435-495 nm; cyan—495-520; green—420-570 nm; yellow—570-590 nm; orange—590-620 nm and red—620-750 nm) or combinations thereof. Or may emit light as a white light (i.e., 380-750 nm).

Although specific wavelength ranges are discussed above, it would be recognized that the wavelength ranges are merely representative as different sources may quote different specific values for the disclosed wavelength ranges.

In addition, the blue light wavelength range may further be considered to comprise the violet wavelength range. For the purposes of this disclosure the term blue light will include the violet color wavelength range.

FIG. 2A illustrates a frontal view of the first exemplary embodiment of the light assembly 110 shown in FIG. 1.

In this illustrated frontal view, lighting elements 112, 114, 116 are shown concentrically oriented about central axis 120 (not shown) at approximately 120 degrees apart from each other. However, it would be understood that the orientation of lighting elements 112-116 with respect to each other about central axis 120 may be determined based on a number of lighting elements.

Further shown are lighting sources 112a, 114a, 116a, within corresponding ones of lighting elements 112, 114, 116. Lighting sources 112a, 114a, 116a may preferably be one of a semi-conductor lasing diode or a semi-conductor non-lasing (e.g., super luminescent) diode.

Although, lighting sources 112a, 114a and 116a are referred to a light emitting diodes (LED) that may be one of a lasing type light emitting diode or of a non-lasing type light emitting diode, other types of lighting sources have been considered and would be within the scope of the claims presented, herewith.

In addition, although described herein as the term lighting emitting diodes or "LED", it would be understood that the term "LED," may comprise a plurality of LEDs arranged in a pattern (e.g., a matrix, circular). Hence, the use of the term "LED," refers to at least one LED.

Lighting sources 112a, 114a, 116a, may be selected to generate and transmit (or emit) light in at least one of the aforementioned wavelength ranges.

FIG. 2B illustrates a frontal view of a second exemplary embodiment of a light assembly 110-1 in accordance with the principles of the invention.

In this second exemplary embodiment lighting assembly 110-1 comprises lighting elements 112, 114, 116, which are similar to those described with regard to FIG. 1 and are oriented linearly along a horizontal line (or a vertical line or a diagonal line, not shown) with respect to the illustrated headset 100. In this second exemplary embodiment, a first lighting element (e.g., 114), may be positioned along central axis 120 (which is not shown but would be understood as projecting substantially perpendicular to the plane of the light assembly 110-1), whereas the remaining lighting elements (e.g., 112, and 116) may be positioned on opposite sides of the centered lighting element 114. In this case, the off-central axis lighting elements (e.g., 112 and 116) may be oriented such that the light generated and emitted by lighting elements 112 and 116 converge on a same point (i.e., point 130) along central axis 120, similar to the manner discussed with regard to FIG. 1.

Figure 3:
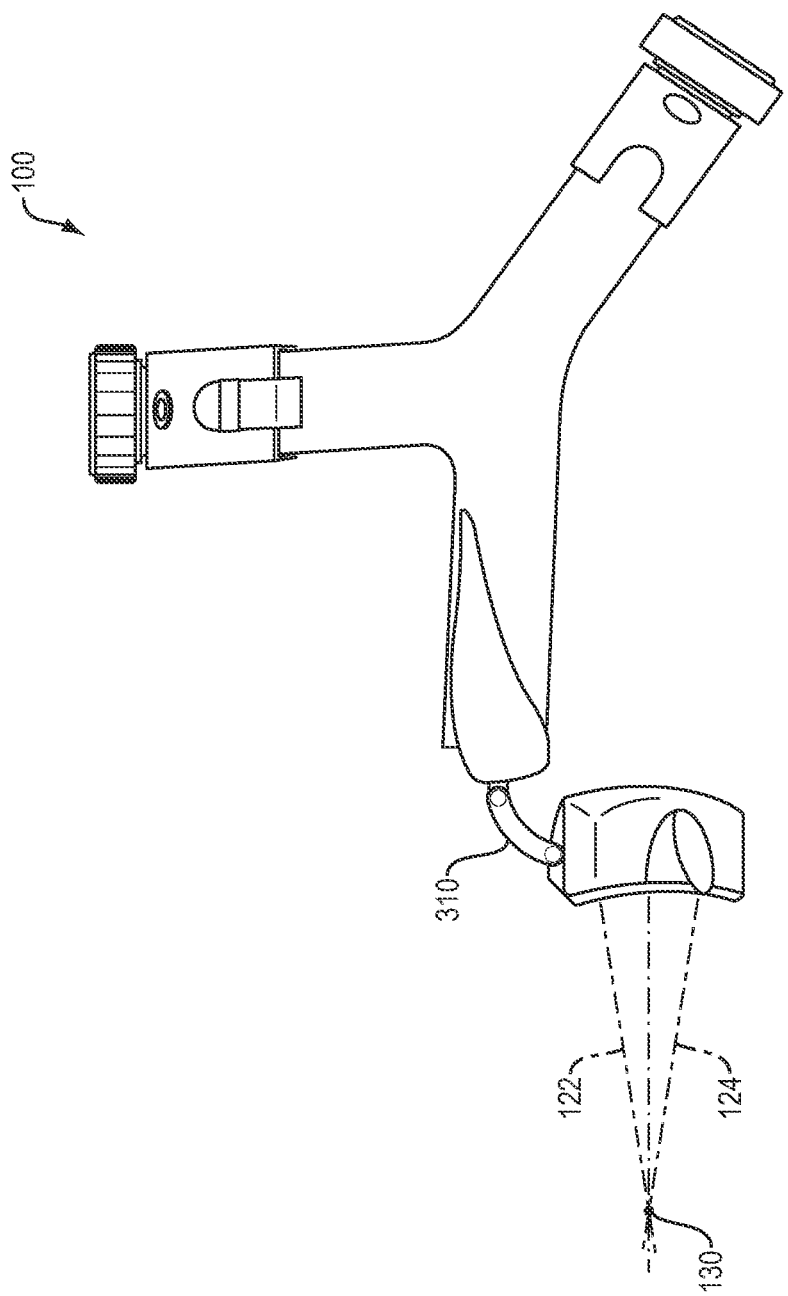
FIG. 3 illustrates a side view of the first exemplary embodiment of the light assembly shown in FIGS. 1 and 2A.

FIG. 3 illustrates a side view of the first exemplary embodiment of the light assembly shown in FIG. 2A.

In this illustrated aspect, light emitted or outputted by the off-central axis lighting elements 112, 114, 116 are shown by dashed lines 122, 124, (126 not shown) converging on a same point 130 along central axis 120 as the lighting sources 112a, 114a, 116a of off-central axis lighting elements 112, 114, 116, respectively, are oriented to project their outputted light toward the viewing point 130.

In addition, light assembly 110 may be retained to head strap 100 by a bracket 310 that allows for the adjustment of light assembly 110 to direct light generated by the lighting elements 112, 114, 116 toward a desired viewing point. That is, the user may determine the orientation of central axis 120 and, consequently, the location of focal (or viewing) point 130.

Figure 4A:
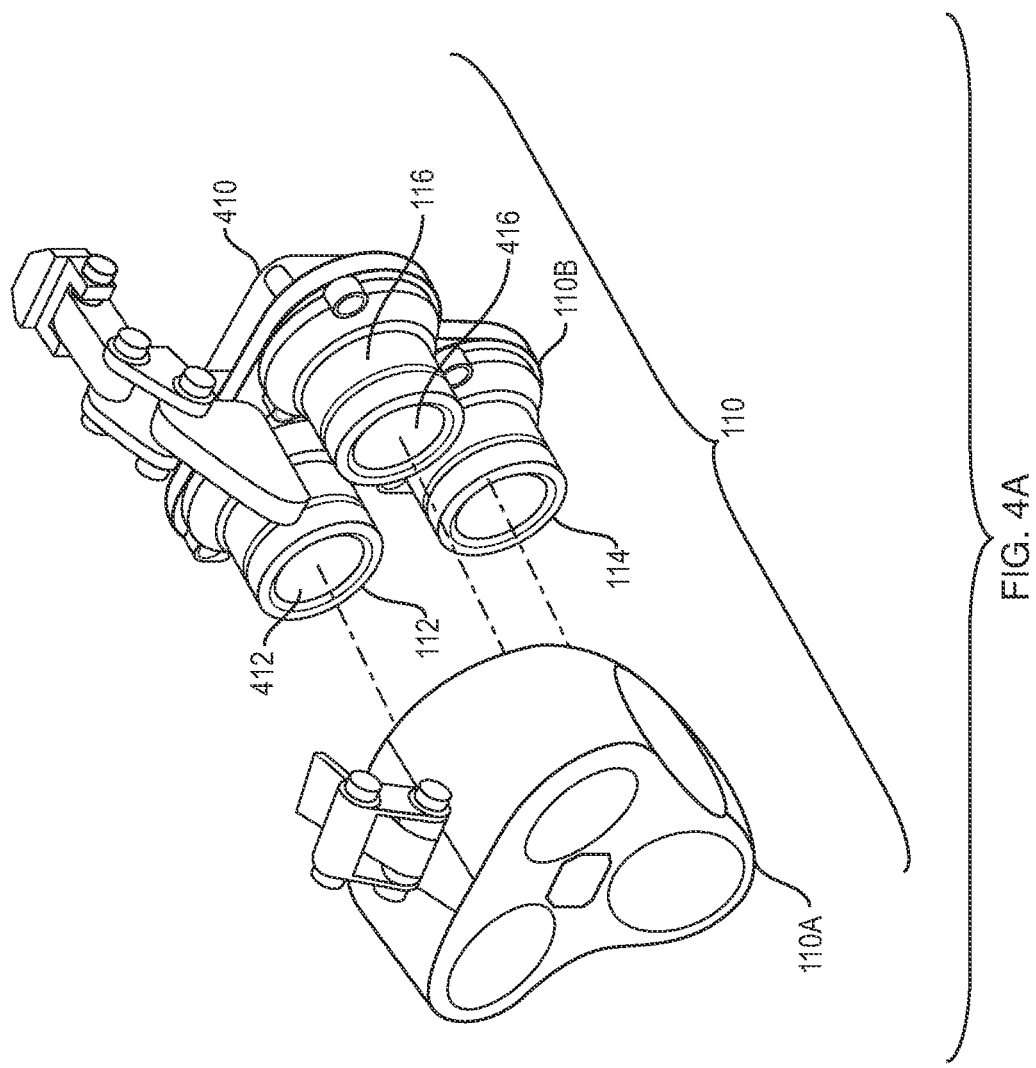
FIG. 4A illustrates an exploded perspective view of the first exemplary embodiment of the light assembly shown in FIG. 2A.

FIG. 4A illustrates an exploded perspective view of the first exemplary embodiment of light assembly shown in FIG. 2A.

In this illustrated exemplary embodiment light assembly 110 comprises a housing 110a and an internal chassis 110b, wherein internal chassis 110b comprises a plurality of lighting elements 112, 114 and 116 positioned on mounting plate 410. Mounting plate 410 provides for the orientation of lighting elements 112, 114, and 116 at an angle such that the light generated by each of the lighting elements 112, 114, 116 converges at a same viewpoint 130 along central axis 120, as previously discussed (see FIG. 1).

Mounting plate 410 may further include a printed circuit board (not shown) including electrical or electronic elements that may control the application of a voltage to light sources, 112a, 114a, 116a, contained within corresponding ones of lighting elements 112, 114, 116.

Lighting elements and lighting sources discussed in U.S. Pat. No. 10,247,384, whose teachings are incorporated by reference, herein, may be utilized for lighting elements 112, 114, 116.

In accordance with an exemplary first aspect of the invention, lighting element 114 may generate a white light as described in U.S. Pat. No. 10,247,384, wherein the light outputted or emitted by lighting elements 112, 114 and 116 is transmitted as a white light.

Further illustrated are filter 412 associated with lighting element 112 and filter 416 associated with lighting element 116. Filters 412 and 416 are selected to limit the light emitted by lighting elements 112 and 116 to known wavelength range.

As filters 412 and 416 remove a portion of the light generated by lighting sources 112a and 116a, respectively, the light outputted by lighting element 112 and 116 is, hereinafter referred to as colored light.

As illustrated, lighting element 114 lacks any filtering and, thus, the light emitted may be considered a white light.

Although the invention has been described with regard to the emission of white and colored light, it would be understood that the light output described, herein, is not the only emitted light configuration considered.

FIG. 4B illustrates an exploded perspective view of a first exemplary lighting element incorporated into light assemblies shown in FIGS. 2A and 2B in accordance with the principles of the invention.

In this exemplary embodiment, which is comparable to the light assembly disclosed in more complete detail in U.S. Pat. No. 10,247,384, light assembly 114 comprises a housing 410 including, therein, a lighting element 114a (not shown) substantially centered on a printed circuit board (not shown) that is retained within housing 410. The printed circuit board (PCB) includes electrical/electronic circuitry that controls the operation of lighting element 114 (e.g., turn on/off). An aperture holder (or plate) 420 and aperture 430, including substantially centered aperture holder passthrough 425 and aperture passthrough 435, respectfully, are further illustrated. Aperture holder passthrough 425 and aperture passthrough 435 are sized to provide for a reduction of stray light emanating from the (not shown) lighting source, as is further discussed in the teaching of U.S. Pat. No. 10,247, 384.

Although aperture holder passthrough 425 and aperture passthrough 435 are shown as comprising a circular form, it would be understood that aperture holder passthrough 425 and aperture passthrough 435 may be in a square or rectangular form. In this case, the square or rectangular form may be sized such that the die portion of a semiconductor diode may be inserted into at least one of aperture holder passthrough 425 and aperture passthrough 435.

Further illustrated is a dome lens 440, that is substantially centered over the passthroughs 425, 435, wherein the lighting source (not shown) is positioned within or at a focal point of dome lens 440. Dome lens 440 provides for the focusing of the light generated by the not shown lighting source.

Lighting element 114 further includes lens assembly 450, which is attachable to housing 410 and used to retain the lighting source (not shown) within the housing 410.

In this illustrated embodiment, housing 410 further includes an internal screw thread 417, that mates to a corresponding screw thread 451 on lens assembly 450 so that housing 410 and lens assembly 450 are rendered as a single unit (e.g., lighting element 114). In accordance with the principles of the invention, the lighting source (not shown) is positioned within the focal length of the objective lens 452, as discussed in USP '384.

Although a screw thread is illustrated, it would be recognized that housing 410 and lens assembly 450 may be joined by other means. For example, housing 410 and lens assembly 450 may be joined together using a bayonet connection, a snap-fit connection, a form fit connection and other similar connections, without altering the scope of the invention.

Further shown, on lens assembly 450, are grooves 454 that substantially circumvent lens assembly 450. Grooves 454, which is an optional feature of lens assembly 450, provide for an increased surface area to distribute heat generated within lighting element 114.

As discussed in U.S. Pat. No. 10,247,384, white light is generated by the combination of a blue light lighting source (i.e., a blue die) and a phosphorus base layer (i.e., a yellowish light) and the use of an appropriately sized aperture passthrough 435 removes stray light associated with the phosphorus base layer from being viewable.

Figure 4C:
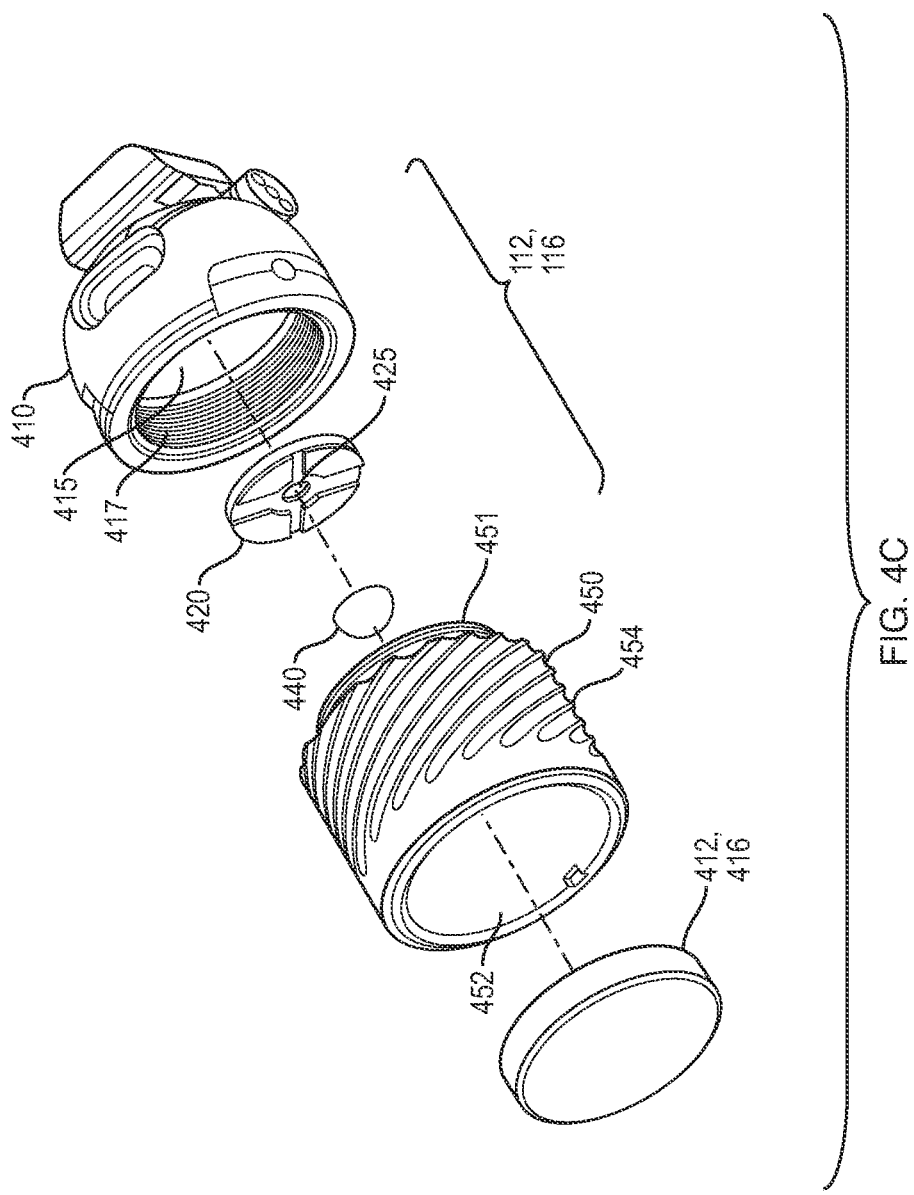
FIG. 4C illustrates an exploded perspective view of a second exemplary lighting element in accordance with the principles of the invention.

FIG. 4C illustrates an exploded perspective view of a second exemplary lighting element incorporated into the light assemblies shown in FIGS. 2A and 2B in accordance with the principles of the invention.

In this illustrated embodiment, which are referred to as lighting element 112 and, 116, lighting elements 112 and 116 comprise elements similar to those disclosed with regard to FIG. 4B (i.e., light source, aperture holder, aperture, dome lens, etc.).

A transmission filter 412 and 416 is further included at a distal end of corresponding one of lighting element 112 and 116, respectively. Filters 412 and 416 are configured to limit the light output of lighting elements 112 and 116 to a known wavelength range.

In accordance with one aspect of the invention, lighting elements 112 and 116 may generate a white light as discussed with regard to FIG. 4B and through the use of filter 412 and 416 may emit a colored light, wherein the specific wavelength range is based on the optical parameters of filters 412 and 416 to block a portion of the generated white light while allowing another portion of the white light to pass.

In accordance with a second aspect of the invention, lighting elements 112 and 116 may comprise a lighting source that generates a light in a desired color wavelength range. In this case, aperture 430 may not be necessary.

FIG. 4C illustrates a second aspect of the invention, wherein aperture 430 is not utilized. However, it would be understood that even with the use of a lighting source generating a light in a desired color wavelength range, aperture 430 may still be utilized.

In accordance with the principles of the invention, lighting element 112 may generate a light in a first colored wavelength range (which for the purposes of explaining the principles of the invention, shall be referred to as first light, hereinafter) and lighting element 116 may generate a light in a second colored wavelength range (which for the purposes of explaining the principles of the invention shall be referred to as second light, hereinafter).

The use of a filtered or color light wavelength output is useful in the medical arts, in that the interaction of the transmission of wavelengths in a range of colored light onto a tissue sample causes the illuminated tissue to generate and emit light (i.e., fluorescence) in a wavelength region that distinguishes normal tissue from diseased tissue.

Figure 5A:
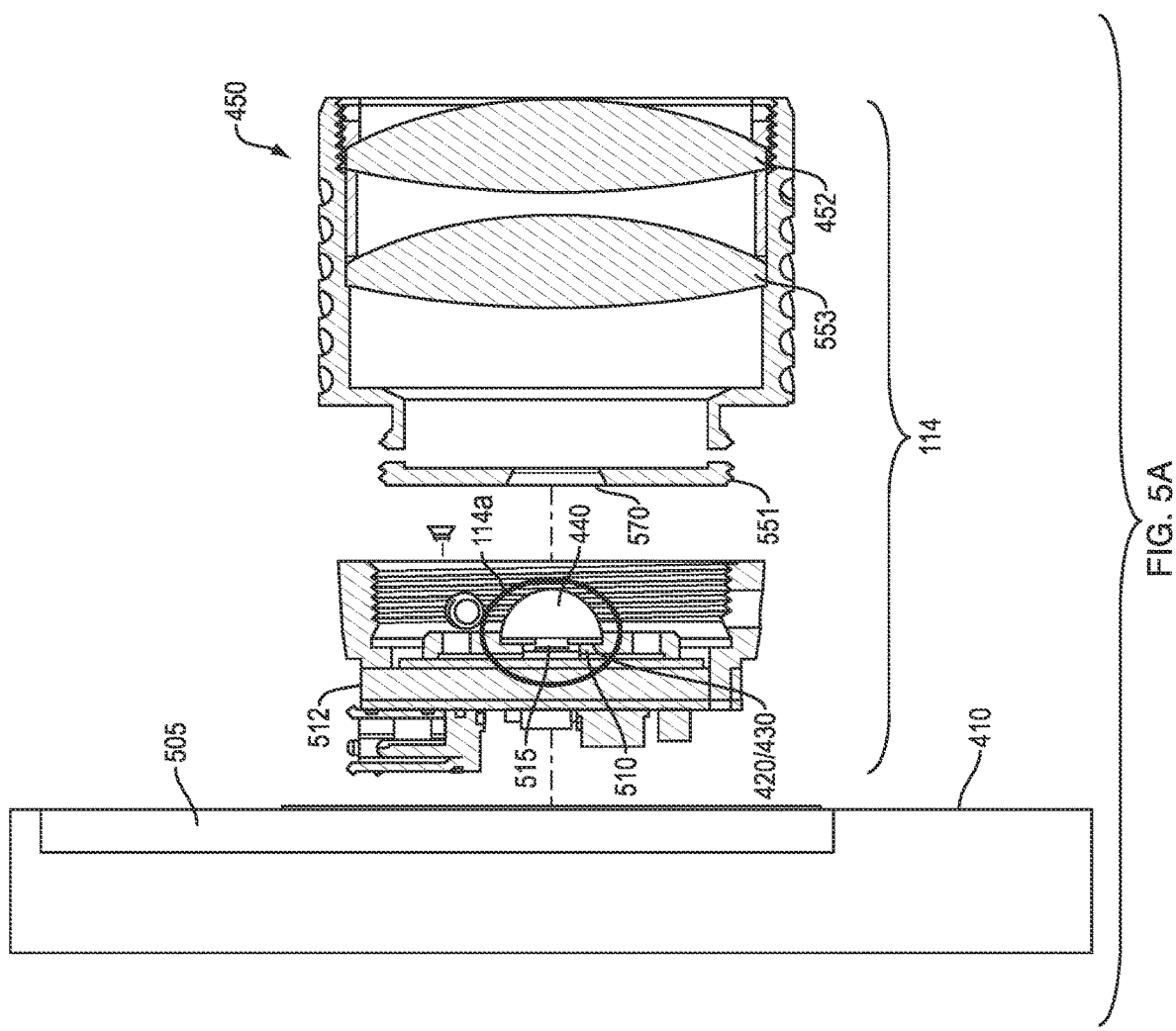
FIG. 5A illustrates a cross-sectional view of the first exemplary embodiment of the lighting element shown in FIG. 4A in accordance with the principles of the invention.

FIG. 5A illustrates a cross-sectional view of the exemplary lighting element shown in FIG. 4A, wherein a white light is outputted In this illustrated exemplary embodiment, which is comparable to the lighting element shown in U.S. Pat. No. 10,247,384, lighting source 114a comprises a lighting device 515 (e.g., a lasing diode or a non-lasing diode) positioned on printed circuit board 512, wherein aperture holder 420/aperture 430 blocks that portion of light produced by lighting device 515, to produce, in this case, a white light.

Further illustrated is a dome lens 440 positioned on aperture 430. Dome lens 440 provides for the focusing of the light outputted by lighting device 515.

Further illustrated is retainer 551, which retains dome lens 440 in position by the contact of a passthrough 570 within retainer 551 through which dome lens 440 is positioned within.

Lighting element 114 further includes housing 450 including objective lens 452. In this illustrated case a second objective lens 553 is shown.

Lighting element 114 is further positioned on mounting plate 410. Mounting plate 410, which as discussed, includes a second printed circuit board 505 (PCB) that controls the application of a voltage to PCB 512 and to lighting source 114a within lighting element 114.

PCB 505 may include resistors, capacitors, diodes and transistors and/or a processor that perform logical operations in the control of a voltage applied to lighting element 114 and subsequently to lighting source 114a. Resistors, capacitors, diodes and transistors and processors are well known elements in the electrical arts. For example, it is known in the art that transistors may operate as switches that direct voltage to, or remove voltage from, an electrical element such as a light emitting diode. Thus, a detailed discussion regarding specific electrical and/or electronic elements is not believed necessary for the understanding of the principles of the invention.

FIG. 5B illustrates a cross-sectional view of the exemplary lighting element shown in FIG. 4C in accordance with the principles of the invention, wherein a colored light is emitted.

In this exemplary cross-sectional view, components similar to those described with regard to FIG. 5A are shown, and a full understand of these components may be obtained from the description provided in FIG. 5A.

Further illustrated is filter 412 (416) positioned at a distal end of the corresponding one of lighting element 112 (116). Filter 412 (416), as discussed, provides for the emission of a light within a known wavelength range, while blocking the emission of light outside the known range.

As discussed with regard to FIG. 4C, the light generated by the lighting source may be a white light or a colored light and filters 412 and 416 may be formulated to emit wavelengths in a desired wavelength range.

Filters 412 and 416 may be formulated using absorptive or reflective properties to block the emission of light generated by a corresponding lighting source 112*a* and 116*a*, respectively. For example, the material (e.g., glass, plastic) of filter 412 may be formulated to increase the absorptive (or the reflective) properties of the material of filter 412 such that light emitted by lighting element 112 above a desired value is blocked. Or the light generated by lighting element 112 may be emitted within a desired wavelength range. Similarly, filter 416 may be formulated (e.g., infused with absorptive matter) to allow the transmission of light within a desired range to be emitted by lighting element 116, while blocking light that is outside the desired wavelength range.

Figure 6:
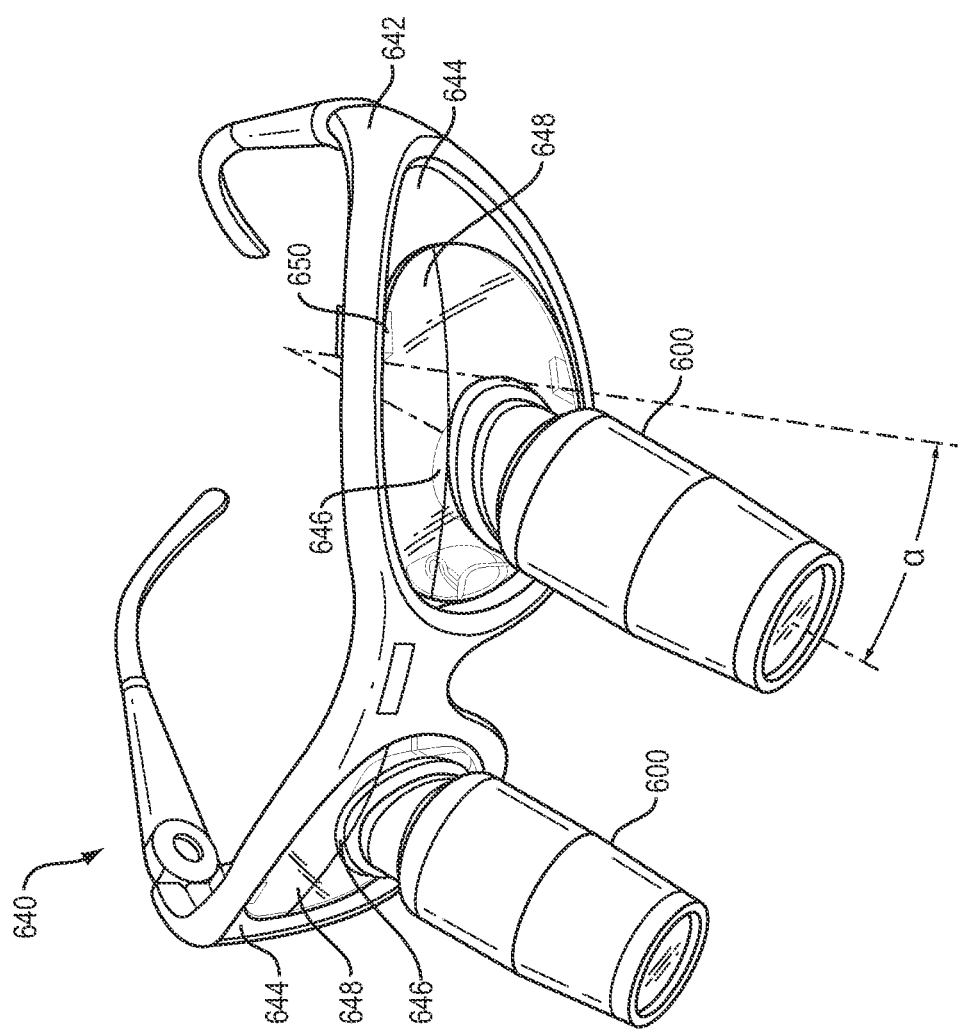
FIG. 6 illustrates a perspective view of an exemplary eyewear device suitable for use in a user wearable visualization system disclosed, herein.

FIG. 6 illustrates exemplary eyewear configuration suitable for use with the light assembly 110 (110-1) shown in FIG. 1 (FIG. 2B) to form a user wearable visualization system, in accordance with the principles of the invention.

In this illustrated example, eyewear or carrier device 640 comprises a frame 642 comprising a plurality of lenses 644. Lenses 644 may be plano or prescriptive, and incorporate therein a lens filtering system 648 configured to prevent the viewing of specific wavelength ranges. Lens filtering system 648 may comprise a coating or a tinting that provides for the filtering of a light presented to lenses 644 such that light within a specific or desired wavelength range is viewed while light beyond the desired wavelength range is blocked from being viewed. In addition, the lens filtering system 648 may be formulated within lenses 644 by the introduction of an optically opaque material into the material of the lenses 644 wherein the optically opaque material increases the optical density of the lenses 644 in a specific wavelength range. Thus, light within the specific range may be prevented from being viewed through lenses 644.

Although lens filtering system 648 is shown as a distinct feature it would be understood by those skilled in the art that the optically opaque material or optical coating or tinting is distributed throughout lenses 644.

In one aspect of the invention, lens filter system 648 is configured to block of light viewed by eyewear 640 in a first wavelength range while allowing light in another wavelength range to pass.

Further illustrated are magnification devices 600, inserted in an aperture 646 within a corresponding one of lenses 644. Magnification devices 600, provide for the magnification of light viewed by magnification devices by a known magnification level (e.g., 2.5×, 3.5×, 4.5×, 6.0×, etc.).

In this illustrated example, the magnification devices 600 are positioned in the lenses 644 at an angle of declination (a) selected to provide a user with ease of use, and to promote proper posture for the back, neck, head, and eyes that may be assumed when working at a close distance.

A magnification filtering system (not shown) may be incorporated into magnification devices 600 to provide for the blockage of light viewed by magnification devices 600 in a first wavelength range while allowing light in second wavelength range to pass.

Figure 7A:
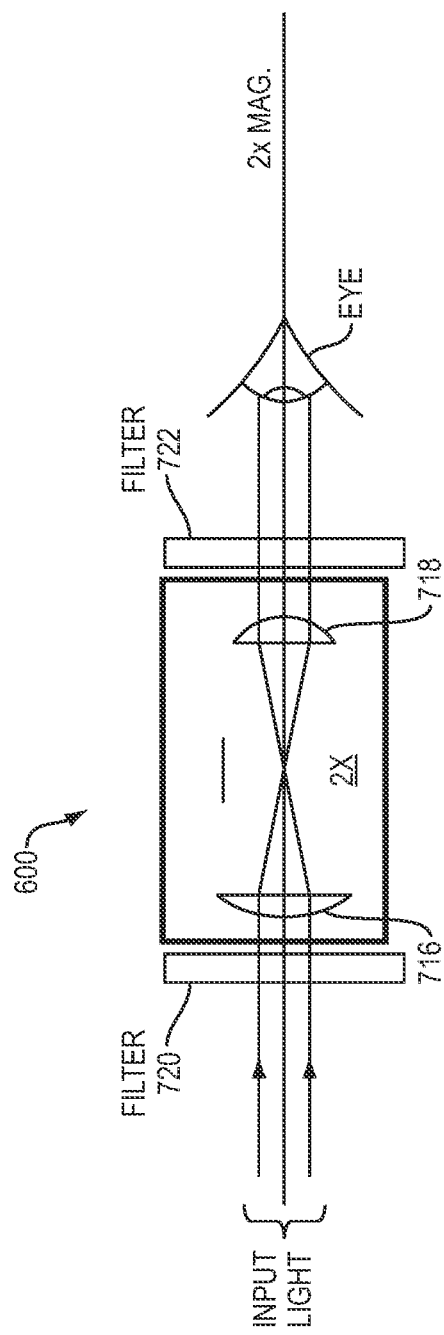
FIGS. 7A and 7B illustrate cross-sectional views of the exemplary configurations of the exemplary magnification device shown in FIG. 6.
Figure 7B:
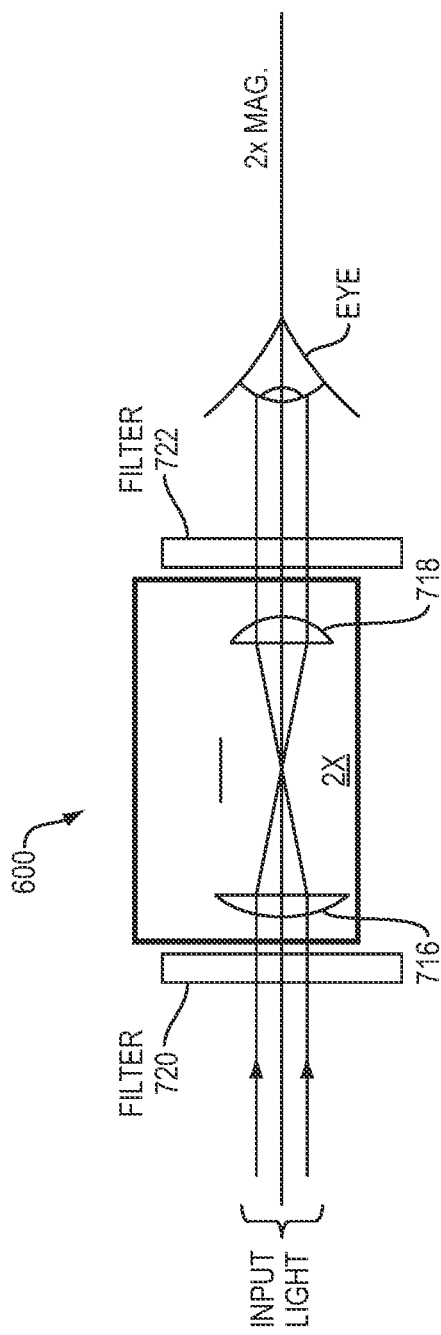

FIGS. 7A and 7B illustrate exemplary embodiments of the filtering system incorporated into magnification devices 600 shown in FIG. 6, wherein FIGS. 7A and 7B illustrate a magnification level of 2×.

Magnification devices 600 comprise an objective lens 716 and an eye lens 718 separated by a known distance. A determination of a magnification level of magnification devices 600 is known in the art to be based on the characteristics of the objective lens 716, the eye lens 718, and the distance separating said objective lens 716 and eye lens 718 and a detailed discussion regarding the determination of magnification level is not believed necessary to recognize the principles of the invention disclosed.

In the exemplary embodiment shown FIG. 7A objective lens 716 and eye lens 718 are separated by a distance that allows for a 2× magnification level. Further illustrated are absorptive filter 720 and absorptive filter 722, wherein filter 720 is positioned at a distal end of magnification device 600, such that light viewed by magnification device 600 enters filter 720 prior to entering magnification device 600.

The filtering characteristics (e.g., optical density) of filter 720 may be formulated to allow passage of wavelengths in a second wavelength range, while blocking wavelengths in the first wavelength range. Similarly, the filtering characteristics of filter 722 may be formulated to block wavelengths in a first wavelength range and allow passage of wavelengths in the second wavelength range.

As discussed with regard to lenses 644, filters 720 and 722 may be formulated such that an optically opaque material may be introduced into the material of the filters 720 and 722 wherein the optically opaque material increases the optical density of filters 720 and 722 in a specific wavelength range. Alternatively, filters 720 and 722 may be constructed using an optical coating or an optical tinting that increase the optical density of filters 720 and 722 in a specific wavelength range.

The filtering characteristics of filter 720 may be determined based at least on the input power of the light being viewed and the magnification level of magnification device 600. Similarly, the filtering characteristics of filter 722 may be determined based at least on the input power, the filtering characteristics of filter 720 and the magnification level of magnification devices 600.

Accordingly, filter 720 reduces an input light to a residual magnification level, which is then magnified by the optical system of magnification device 600. Filter 722 is then formulated to reduce the magnified residual light to a level that prevents damage to a user's eye caused by either the viewed light wavelength or the power of the viewed light.

FIG. 7B illustrates a similar configuration of magnification device 600. In this case, the filtering capability of reflective filters 720 and filters 722 are based on the ability of the filters to prevent the passage of light in an undesired range (i.e., a first wavelength range) and allow passage of light in the second wavelength range.

Filters 720/722, whether absorptive or reflective, operate in a similar manner to reduce the magnitude of the input light to a level that prevents damage to the eyes of a user.

Although filters 720 and 722 are shown, it would be recognized that the filtering capability of magnification devices 600 may be performed using a single filter, which may be positioned prior to the objective lens 716 or post the eye lens 718. The use of a single filter may the determined based in part on the input power of the light viewed by the magnification devices 600 and the magnification level of magnification devices 600.

Similarly, while two absorptive and two reflective filters are shown, it would be recognized that the specific filter combination is not limited to the illustrated examples. For example, the filter system 720/722 may comprise an absorptive filter and a reflective filter wherein the filter pass band characteristics may be similar. That is, block wavelengths of a first light wavelength range through a process of absorbing and then reflecting light in the first light wavelength range.

In one aspect of the invention, wherein light assembly 110 transmits a first light and a second light, the filtering capabilities of filters 720/722 and filter system 648 may be formulated based on the wavelength ranges of the transmitted first light and the second light, the expected input power of the light to be viewed, and the magnification level of the level of magnification of the light to be viewed.

FIG. 7C illustrates a graph for an exemplary filtering capability of the eyewear 640 and magnification devices 600 shown in FIG. 6 in accordance with the principles of the invention.

In the illustrated graph, wavelength is measured along the horizontal axis, light intensity is measured on the left vertical axis and the filter response characteristic 780 of lenses 644 and magnification devices 600 is measured along the right vertical axis.

In this illustrated example, a first light 750 is shown at a first wavelength with an emitted light intensity of 1.0 and a second light 760 is shown at a second wavelength with an emitted intensity less than that of the intensity of the first light 750.

Further illustrated is a generated fluorescent light 770 at a wavelength higher than the second light 760. The intensity of fluorescent light 770 is determined based on the emitted light intensities of first light 750 and second light 760 and the degree of interaction between the first light 750 and the second light 760 with the tissue. Fluorescent light 770 may be generated by the interaction of the emitted first light 750 and second light 760 with bacteria or other inflammation that may be associated with diseased tissue.

Further illustrated is the filter response characteristics 780 of lens 644 and magnification devices 600, wherein filter response characteristic 780 is shown providing for the passing (i.e., transmission) of second light 760 and fluorescent light 770.

In accordance with the principles of the invention, transmission filters 412 and 416 associated with lighting elements 112, 116, respectively, may be formulated to cause the emission of first light 750 and second light 760, respectively, about the illustrated nominal wavelengths. That is, the transmission filter characteristic of filters 412 may be formulated to allow emission of light generated by lighting source 112a to be limited to a wavelength associated with first light 750. For example, where lighting source 112a may generate a light in a wavelength range of 400 nm to 450 nm, the transmission filter characteristics of filter 412 may be selected or formulated to limit the light emitted by lighting element 112 to be within a range of 430-440 nm (i.e., a nominal value of 435 nm). Similarly, the filter characteristics of transmission filter 416 may be formulated to limit the light generated by lighting source 116a to be limited to a wavelength associated with second light 760. For example, where lighting source 116a generates a white light (i.e., 385-700 nm) the filter characteristics of filter 416 may be selected or formulated to limit the light emitted by lighting element 116 to be within a range of 460-480 (i.e., a nominal value of 470 nm). Thus, the filter characteristic of filters 412 and 416 may be selected to pass or emit wavelengths of light in a desired wavelength range while blocking or suppressing the emission of wavelengths outside the desired wavelength emission range.

The filter characteristics of filters 412 and 416 may be further formulated to remove emitted wavelengths below an expected power or intensity level of the nominal wavelength, for example.

In this illustrated example, the filter characteristics of filter 412 are further formulated to prevent or cutoff, the emission of light, which is represented as dashed line 754, associated with first light above a specified wavelength value. Similarly, the filter characteristics of filter 416 are formulated to prevent or cutoff, the emission of light, which is represented as dashed line 764, above a specified wavelength value.

In this illustrated example, the light emission cutoff values 752 and 754 associated with first light 750 and second light 760, respectively, may be determined based on an intensity value. For example, cutoff value 752 may be selected to prevent wavelengths in a wavelength band or range associated with first light 750 having an intensity (or power) level less than a known percent (e.g., 1%, 5%, 10%, etc.) of the intensity (or power) output of the nominal wavelength of first light 750. Similarly, light emission cutoff value 762 may be selected to prevent wavelengths in a wavelength band associated with second light 760 having an intensity level less than a known percent (e.g., 1%, 5%, 10%, etc.) of the intensity output of the nominal wavelength of second light 760.

In one aspect of the invention, light emission cutoff value 752 may be selected such that wavelengths associated with first light 750 having an intensity less than an intensity of second light 760 may be prevented or blocked from being emitted.

In one aspect of the invention, the intensity of the first light at viewpoint 130 may be significantly greater that the intensity of the second light. For example, the intensity of light outputted by the first lighting source 112a and the intensity of light outputted by the second lighting source 116a may be adjusted based on a drive current provided to the first lighting source 112a and the second lighting source 116a.

In this illustrated example, the light intensity of the first light is significantly higher than the light intensity of the second light.

Further illustrated is the filter response 780 of the filtering system 648 of lenses 644 and filters 720/722 of magnification devices 600, shown in FIG. 6, that provides for the blocking and passage of the light presented to lenses 644 and magnification devices 600.

In this illustrated example, the lens filtering system 648 and the magnification filter system 720/722 are configured, through the appropriate selection of corresponding filter characteristics (i.e., optical density), to attenuate light having wavelengths below a specific wavelength value 740 while allowing light above the specific wavelength value 740 to pass.

That is, the filter response characteristic 780 (i.e., the optical passband) extends from a wavelength 740, which is situated between the wavelength of first light 750 and the wavelength of second light 760 and increases to allow substantially 100 percent of second light 760 and fluorescent light 770 to be viewable through the filter system 648 of lens 644 and filters 720/722 of magnification 600, whereas the wavelengths associated with first light 750 are prevented from being viewed through the lenses 644 and magnification devices 600.

Although, the filter response characteristic of the filter system 648 of lens 644 and filters 720/722 of magnification lens 600 are shown as being the same, it would be recognized that the filter response characteristics of filter system 648 of lens 644 and filters 720/722 of magnification lens 600 may be chosen to provide for different response characteristics. For example, the filter response characteristic of filter system 648 of lens 644 may be selected to allow for only the viewing of fluorescent light 770 while the filter response characteristic of filters 720/722 may be selected to allow for the illustrated response characteristics 780.

In accordance with the principles of the invention, a user wearable fluorescent light visualization system disclosed provides for the emission of light and the subsequent viewing of a light (i.e., a fluorescent light) generated through the interaction of the emitted light with an object, such as a tissue, while preventing the viewing of portions of the emitted light that may be harmful to a user and/or interfere with the viewing of the generated fluorescent light.

Thus, in accordance with a first exemplary embodiment of the invention, utilizing the head strap 100 and the light assembly 110, shown in FIG. 1, and the eyewear device 640 shown in FIG. 6, light generated and emitted by light assembly 110 and reflected by an object (tissue) toward lenses 644 may be selectively viewable through lenses 644, such that the first light 750 portion of the emitted light is removed from the reflected light while allowing a second portion of the reflected light (i.e., second light 760 and fluorescent light 770) to be viewable. And, thus, provide a practitioner the ability to safely distinguish, in real-time, healthy tissue from diseased tissue through the viewing of the received fluorescent light.

In addition, the selection of the illustrated filter response 780 further provides for the viewing of a white light generated by lighting element 114 to be viewed as a substantially white light as the pass band characteristics 780 allows a significant number of wavelengths to be viewed.

Although the first exemplary embodiment discussed above includes magnification devices 600, it would be understood that the eyewear 640 may be utilized to view the fluorescent light generated by the bacteria within the diseased tissue without including the magnification devices 600.

In accordance with another aspect of the invention, the use of an enhancing agent, such as a fluorophore may increase the ability of the practitioner to distinguish healthy tissue from diseased tissue as the diseased tissue absorbing the fluorophore increases the generation of the florescent light caused by the interaction of the transmitted first light and/or second light with the fluorophore.

In addition, other enhancing agents, such as a dye or a contrasting agent, may be utilized to enhance the generation of fluorescent light to highlight differences between diseased tissue and healthy tissue.

In one aspect of the invention, the contrasting element (or dye or fluorophore) may be applied directly to the suspected diseased tissue area. In another aspect of the invention, the dye, fluorophore or contrasting element may be injected into a patient, wherein the injected element may be absorbed or "taken up" by the tissue. In still a further aspect of the invention, the dye, fluorophore or contrasting agent may be orally ingested by a patient, such that the dye, fluorophore or contrasting agent may be absorbed or "taken up" by the tissue.

Accordingly, with the application or the use of a contrasting agent, dye, or fluorophore (e.g., aminolevulinic acid HCL (which is referred to in the art as 5-ALA)), the generated fluorescent light 770 may provide a further distinction between healthy and diseased tissue. Aminolevulinic acid HCL, is marketed under the brand name Gleolan. Gleolan is a trademark of NX Development Corp.

Figure 8:
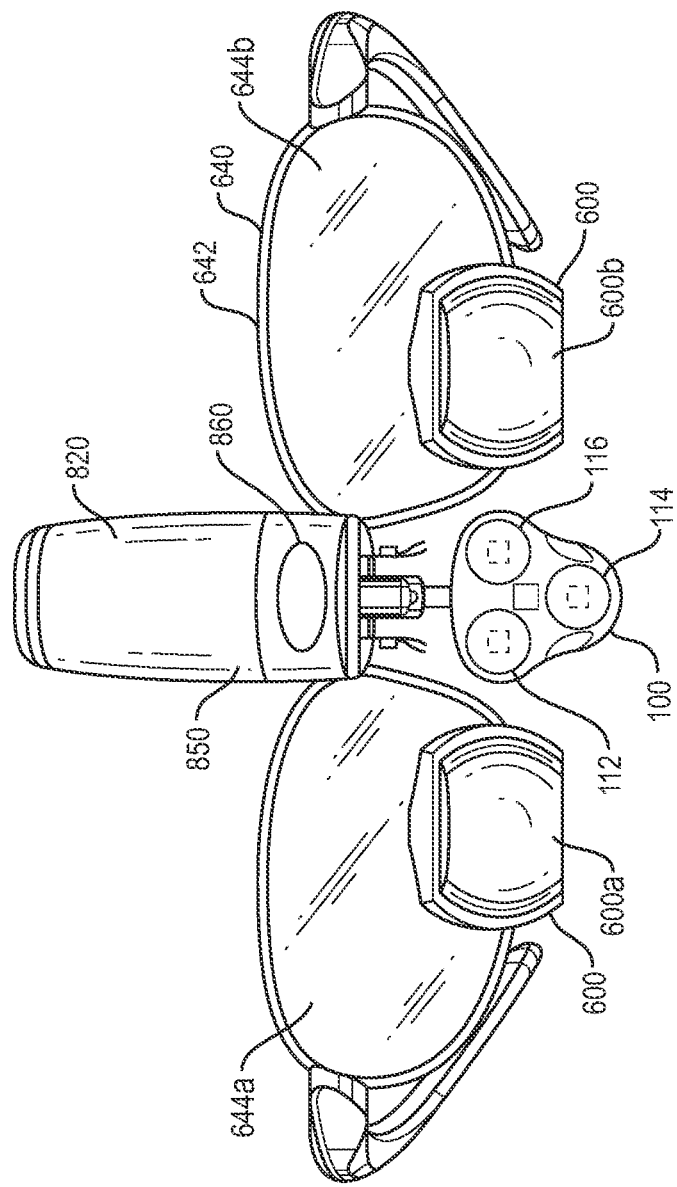
FIG. 8 illustrates a front view of a second exemplary embodiment of a visualization system in accordance with the principles of the invention.

FIG. 8 illustrates a frontal view of a second exemplary embodiment of a visualization system in accordance with the principles of the invention.

In this illustrated second exemplary embodiment, a carrier device similar to that disclosed with regard to FIG. 6 is illustrated and a full understanding of these elements presented in FIG. 8 may be obtained from the descriptions provided in FIGS. 1 and 6.

Further illustrated is light assembly 110 (see FIG. 1), comprising lighting elements 112, 114, 116, positioned between magnification devices 600.

Although, this second exemplary embodiment is shown utilizing the magnification devices 600 of FIG. 6, it would be understood, the magnification devices 600 are not necessary for viewing the generated fluorescent light.

In this illustrate example, pod 820 contains a power source (i.e., a battery) that may be used to power the lighting sources 112a, 114a, 116a within lighting elements 112, 114, 116, respectively, and other electronic circuitry (not shown) that is used to control a voltage (or current) applied to the lighting source 112a, 114a, 116a.

Further illustrated is a contact or contactless control means 860 for controlling the application of a voltage or current to any of lighting sources 112a, 114a, 116a.

For example, the control means 860 may be configured to allow for a capacitive touch of metallic elements on pod 820 to apply/remove the voltage or current applied to one or more of the lighting sources 112a, 114a, 116a. In another aspect of the invention, control means 860 may be configured to allow for a non-contact control of the voltage (or current) applied to the lighting sources 112a, 114a, 116a. (see, U.S. Pat. No. 10,240,769).

For example, a non-contact control of the voltage (or current) applied to lighting sources 112a, 114a, 116a may be achieved by the occurrence of a detection of a reflection of a signal, such as an infra-red, or an ultra-sonic, signal, that may be transmitted through a transmitter (not shown) and which is reflected by an object passing through the transmitted signal. A reflection of the transmitted signal may be detected by a receiver (or a detector, not shown). The receiver or detector may then generate an indication of the reflected signal to the electronic circuitry to apply or remove the voltage to the lighting sources 112a, 114a, 116a.

Although the power source is shown attached to the eyewear, it would be recognized that the power source may be separated from the eyewear and those skilled in the art would have the knowledge to alter the configuration shown, herein, to provide power from a remote source to the lighting sources 112a, 114a, 116a without undue experimentation.

Figure 9:
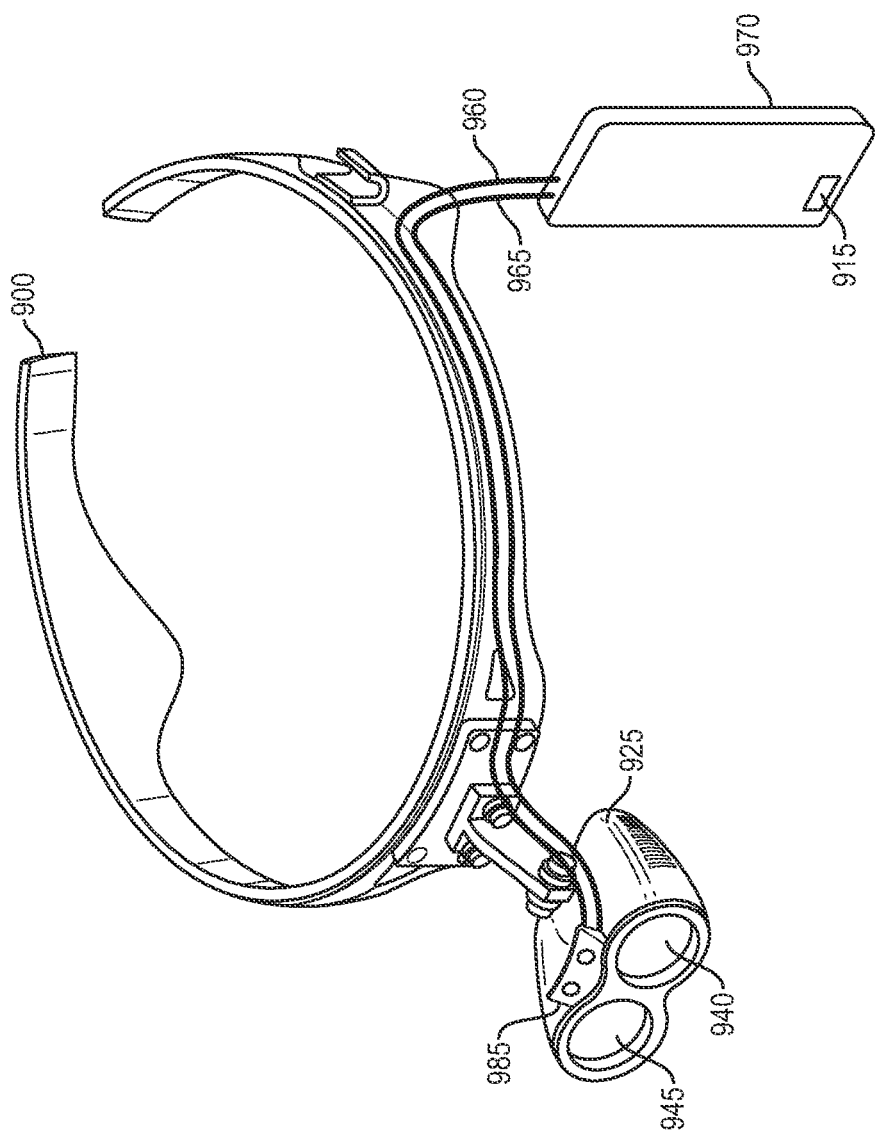
FIG. 9 illustrates a perspective view of a third exemplary embodiment of a lighting assembly in accordance with the principles of the invention.

FIG. 9 illustrates a perspective view of a third exemplary embodiment of a lighting assembly 925 in accordance with the principles of the invention.

In this illustrated exemplary third configuration, light assembly 925 comprises two lighting elements 940, 945, shown suspended from head band 900, which allows for the retention of light assembly 925 to a user. The head band in this illustrated embodiment is similar to that shown in RE456,463, the contents of which are incorporated by reference, herein.

Each of the two lighting elements 940, 945 is capable of generating light in a plurality of wavelength ranges, as will be discussed. Further illustrated is an electrical source 970 (e.g., a battery pack), remotely located from light assembly 925. Electrical source 970 provides electrical energy to the lighting sources (not shown) within lighting elements 940, 945. In this illustrate embodiment, electrical energy from power source 970 is provided to lighting elements 940, 945 through one or more wired connections, 960, 965.

Further illustrated is a switch 915 that may operate to determine which of the multiple lighting sources within lighting elements 940, 945 generate a light. Alternatively, light assembly 925 may include a contact or contactless switch control 985, which may utilize a capacitive touch or a contactless (i.e., infra-red transmission/receiving system) to alter the output of light from corresponding ones of lighting elements 940, 945. Contact and contactless switch control 985 is similar to the contact and contactless switch control previously discussed with regard to FIG. 8.

Figure 10A:
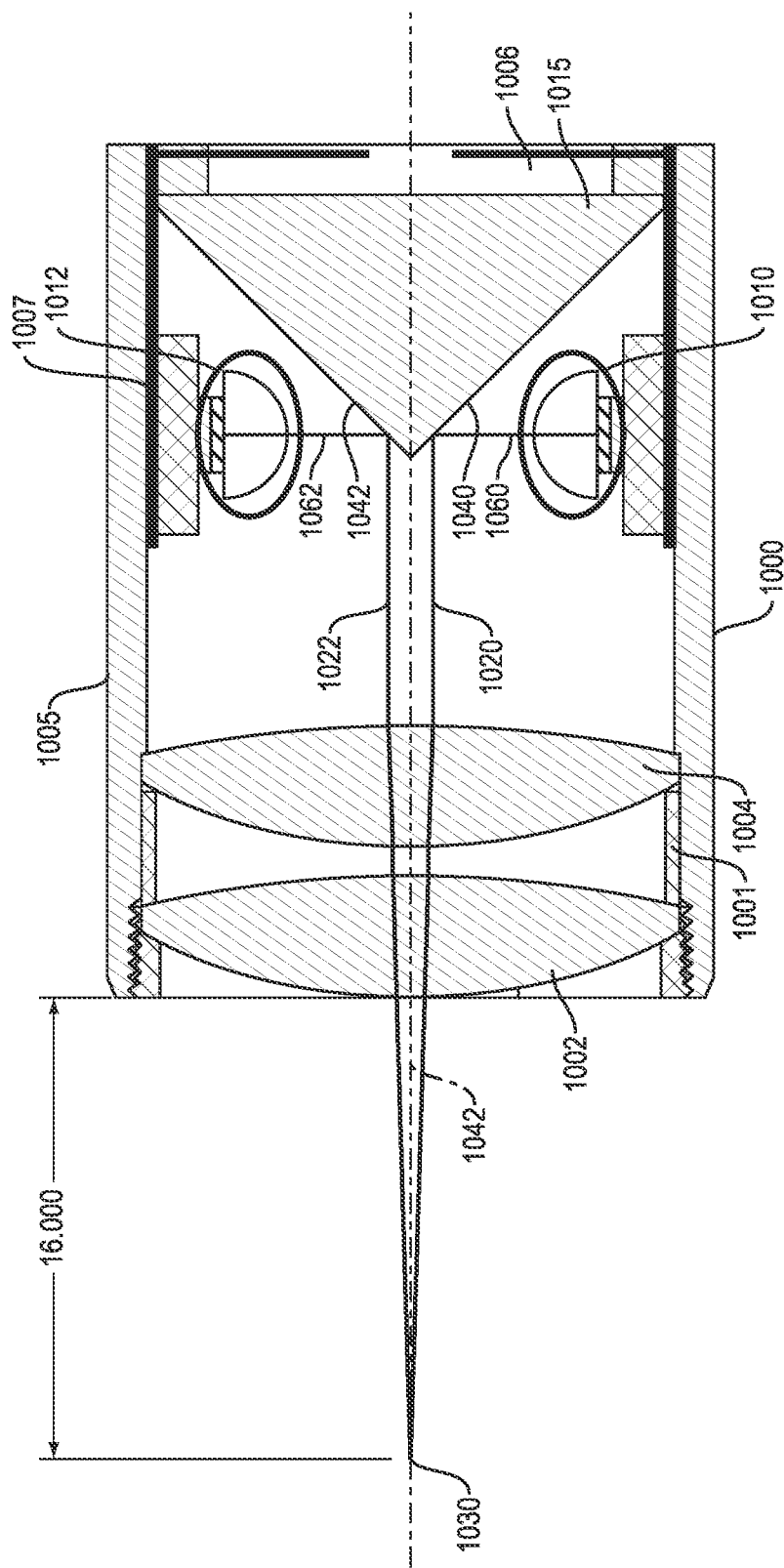
FIG. 10A illustrates a cross sectional view of a first aspect of a third exemplary embodiment of a lighting element in accordance with the principles of the invention.

FIG. 10A illustrates a cross sectional view of a first aspect of a third exemplary embodiment of a lighting element in accordance with the principles of the invention.

In this exemplary embodiment, each of lighting elements 940 and 945 comprises housing 1000 and lens assembly 1001 positioned on a first end of housing 1000. Lens assembly 1001 comprises at least one lens 1002, 1004 forming an optical axis 1042 on which is focal point 1030. As would be recognized, housing 1000, lens assembly 1001 and lens 1002, 1004 are comparable to housing lens assembly 450, and lens 454, 553, shown in FIGS. 4 and 5A, for example. Similarly, focal point 1030 is similar to viewpoint 130 shown in FIG. 1.

Further illustrated is optical assembly 1007 comprising a plurality of lighting modules (illustrated as first lighting module 1010 and second lighting module 1012) positioned around an inner circumference of optical assembly 1007

The first lighting module 1010 and second lighting module 1012 are similar in construction to lighting element 114a, shown in FIGS. 4A, 5A, wherein a white light is generated.

Although only two lighting modules are shown, it would be understood that a plurality of lighting modules may be incorporated about the internal circumference of optical assembly 1007.

Optical assembly 1007 further comprises a light director 1015, which operates to redirect light generated by first lighting module 1010 and second lighting module 1012 toward lens assembly 1001.

Further illustrated is light director 1015 constructed as one of a pyramid or a cone shaped element positioned on base 1006.

Although, a pyramid is discussed for the configuration of light director 1015, it would be recognized that the three-dimensional shape of light director 1015 may comprise a multi-sided structure (i.e., with a geometrically shaped base such as a triangle, a square, a pentagon, etc.) with sloping sides that meet in a point at the top, wherein the number of sides of the structure is based on a number of lighting sources positioned about the inner circumference of optical assembly 1007. In another aspect of the invention, light director 1015 may comprise a cone, wherein the base is circular with sloping sides that meet in a point at the top.

In this illustrated example, light director 1015 extends from base 1006 at an angle that is oriented at a substantially 45-degree angle with respect to optical axis 1042, to enable light generated by first lighting element 1010 and second lighting element 1012 to be redirected toward lens assembly 1001.

Light director 1015 further comprises reflective surfaces (e.g., polished aluminum, mirror, etc.) 1040, 1042, which operate to increase the amount of light generated by first lighting module 1010 and second lighting module 1012 that is reflected toward lens assembly 1001.

As illustrated, light generated by first lighting module 1010 is directed along light path 1060 and impinges upon reflective surface 1040. Reflective surface 1040 redirects the light along light path 1020 toward lens assembly 1001.

Similarly, light generated by second lighting module 1012 is directed along light path 1062 and impinges upon reflective surface 1042. Reflective surface 1042 redirects the light along light path 1022, toward lens assembly 1001 substantially parallel to optical axis 1042.

In accordance with the principles of the invention, light directed along light paths 1020 and 1022 is outputted by lens assembly 1001 such that the light converges onto known point 1030 (i.e., focal point 130, FIG. 1). In this illustrative example, the focal point 130, which is represented as 1030, is selected to be approximately 16 inches from a lighting device 1000.

Figure 10B:
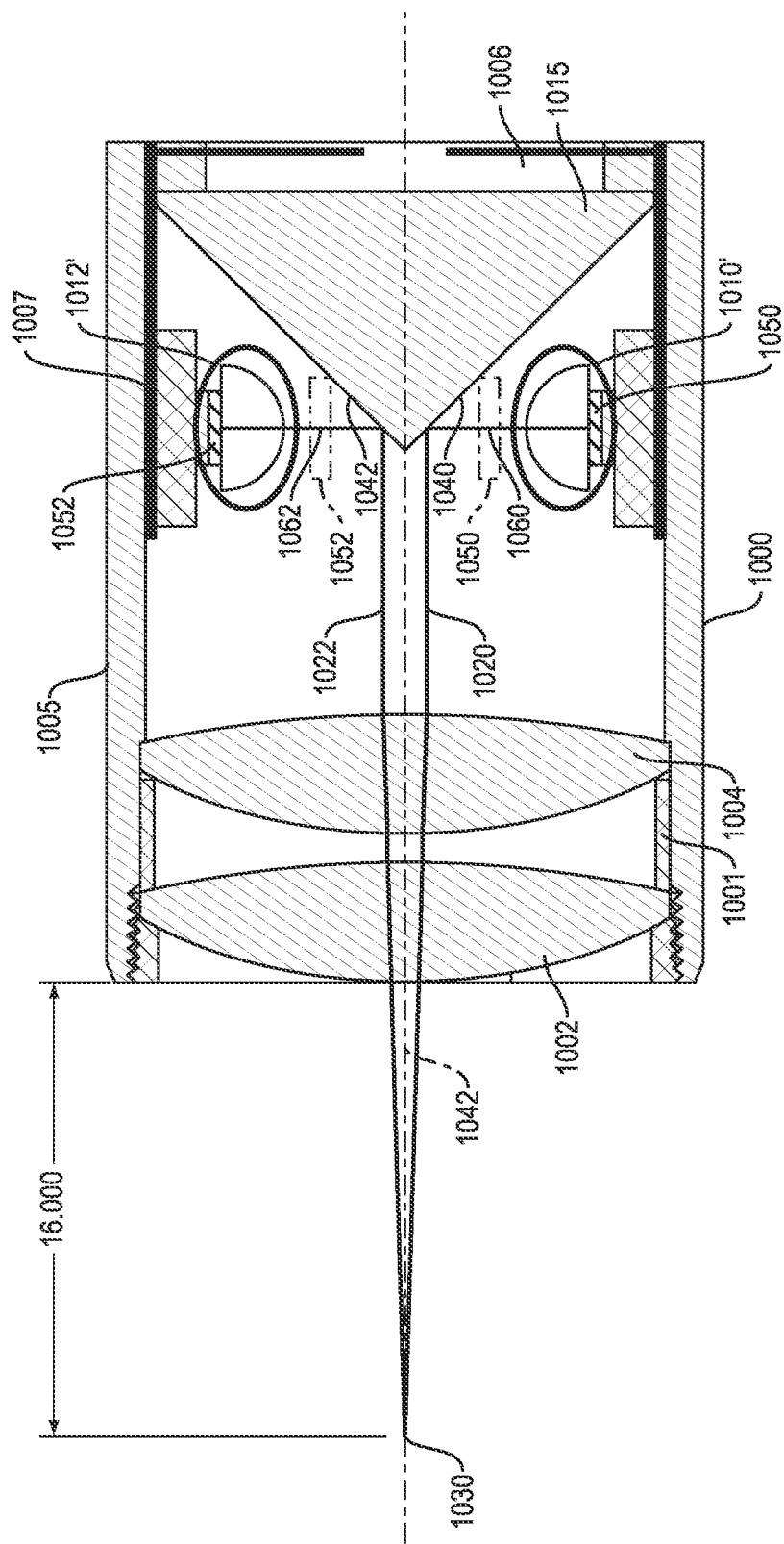
FIG. 10B illustrates a cross sectional view of a second aspect of the third exemplary embodiment of a lighting element in accordance with the principles of the invention.

FIG. 10B illustrates a cross sectional view of a second aspect of the third exemplary embodiment of lighting element shown in FIG. 10A.

Lighting elements 940, 945 include elements that are comparable to those disclosed with regard to FIG. 10A and a full understanding of these components may be obtained from the description provided in FIG. 10A.

FIG. 10B further illustrates first lighting element 1010' and second lighting element 1012', that are comparable to first lighting element 1010 and 1012, respectively.

However, first lighting element 1010' includes filter 1050 and second lighting element 1012' includes filter 1052, wherein filters 1050 and 1052 are comparable to at least one of filter 412 and 416, to limit the light transmitted by first lighting element 1010' and second lighting element 1012' to a known wavelength (e.g., first light or second light) or a desired wavelength band.

For example, filter 1050 may operate in a manner similar to that of filter 412 to filter the light generated by lighting element 1010' to a first light wavelength range (e.g., first light 750) and filter 1052 may operate in a manner similar to that of filter 416 to filter the light generated by lighting element 1012' to a second light wavelength range (e.g., second light 760).

In the illustrated embodiment, filters 1050, 1052, are shown positioned between the dome lens 440 and the lighting source. However, in a second aspect of the invention, the filters 1050 and 1052 may be positioned after light passes through dome lens 440. FIG. 10B further illustrates the optional position of filters 1050, 1052 as dashed lines.

Figure 11A:
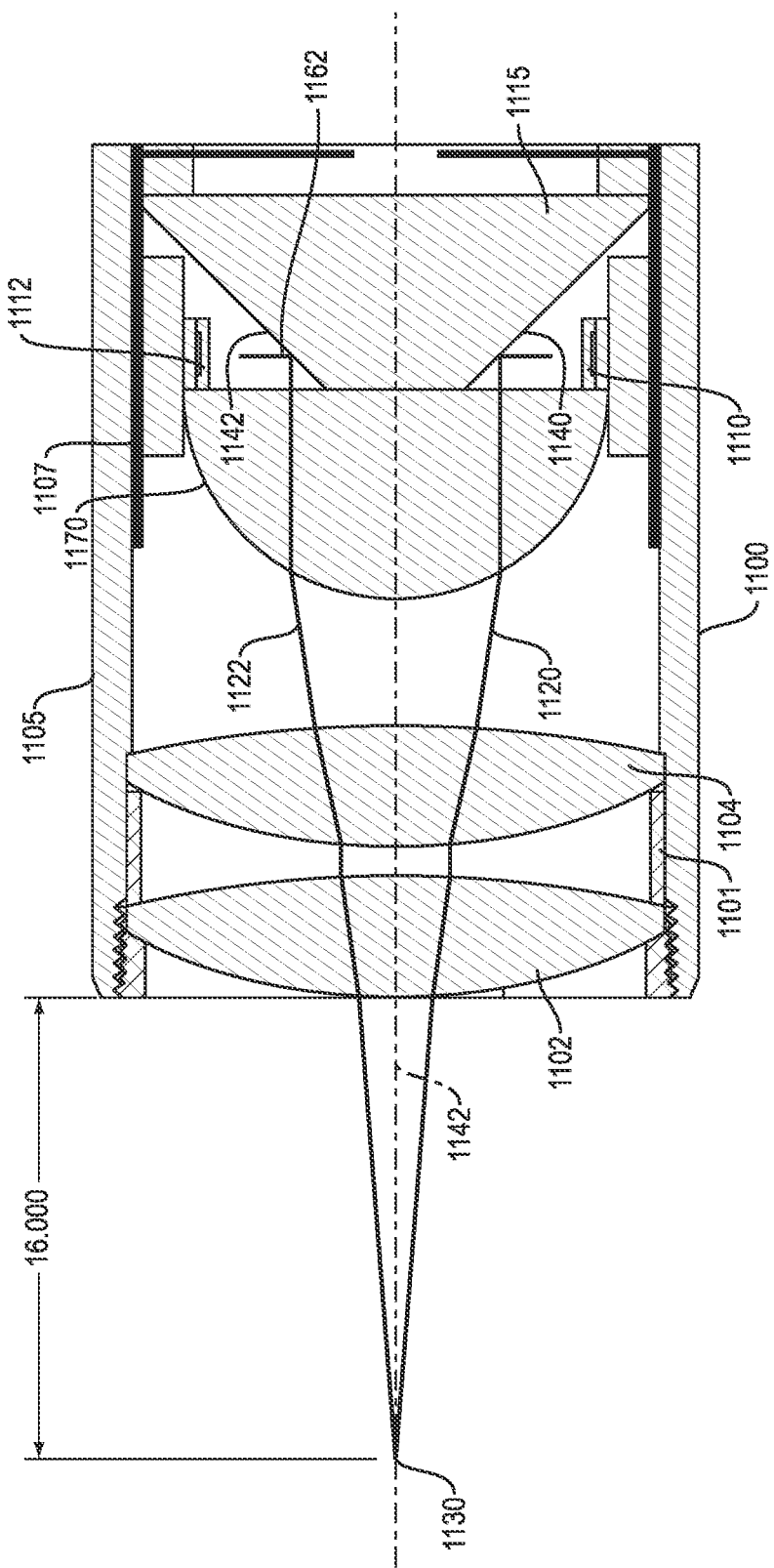
FIG. 11A illustrates a cross sectional view of a first aspect of a fourth exemplary embodiment of a lighting element in accordance with the principles of the invention.

FIG. 11A illustrates a cross sectional view of a first aspect of a fourth exemplary embodiment of a lighting element in accordance with the principles of the invention.

In this exemplary embodiment, each of lighting elements 940 and 945 comprises elements similar to those described with regard to FIG. 10A and a full understand of these elements may be obtained from the description provided in FIG. 10A.

In this illustrated case, first lighting element 1110 and second lighting element 1112 are similar in construction to lighting element 1010 and 1012, respectively and are similarly positioned about an inner circumference of housing 1100.

However, first lighting element 1110 and second lighting element 1112 lack dome lens 440 associated with first lighting element 1110 and second lighting element 1012. In this case, first lighting element 1110 and second lighting elements 1112 comprise a light emitting source (e.g., an LED) and an aperture (not shown) to limit the output of first lighting element 1110 and second lighting element 1112 to a white light wavelength range.

Further illustrated is lens 1170 positioned substantially perpendicular to optical axis 1142. In this illustrated example, lens 1170 is positioned in contact with light director 1115, which is shown as a clipped or truncated pyramid, and is sized such that light generated by lighting sources 1110 and 1112 is redirected from reflective surfaces 1140, 1142 and is captured by lens 1170.

As discussed with regard to FIGS. 10A and 10B, light generated by first lighting element 1110 and second lighting element 1112 is directed to focal point 1130.

Figure 11B:
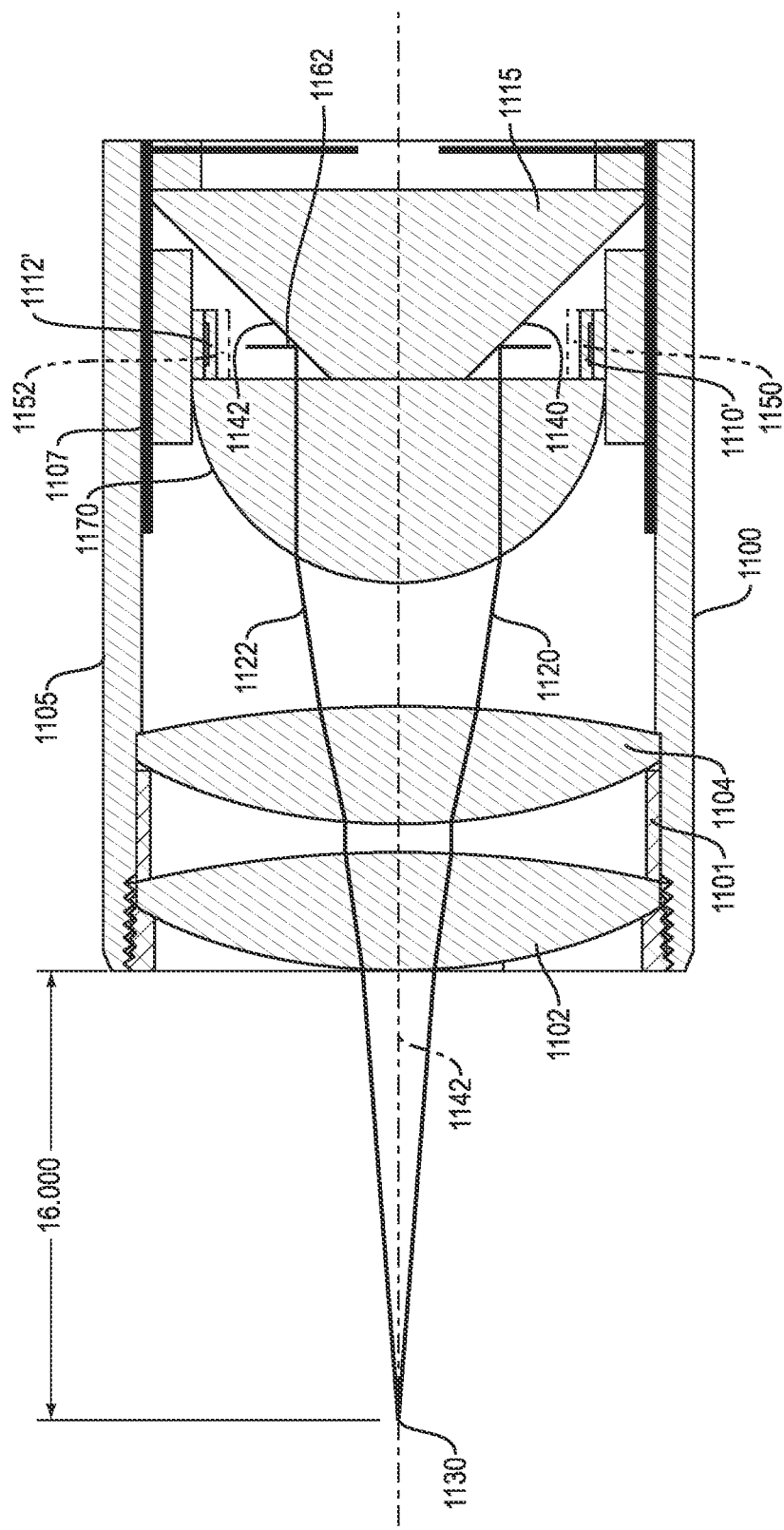
FIG. 11B illustrates a cross sectional view of a second aspect of a fourth exemplary embodiment of a lighting element in accordance with the principles of the invention.

FIG. 11B illustrates a second aspect of the fourth exemplary embodiment of the lighting element shown in FIG. 11A.

In this second aspect of embodiment of lighting elements 940, 945, lighting elements 940, 945 comprise elements that are comparable or similar to those described with regard to FIG. 11A and, thus, a detailed discussion of comparable elements is believed not necessary for the understanding of the principles of the invention claimed.

FIG. 11B further illustrates filter 1152 associated with lighting element 1112' and filter 1150 associated with lighting element 1110', wherein filters 1150 and 1152 are comparable to at least one of filter 412 and 416, as discussed with regard to filters 1050 and 1052, respectively.

Figure 12A:
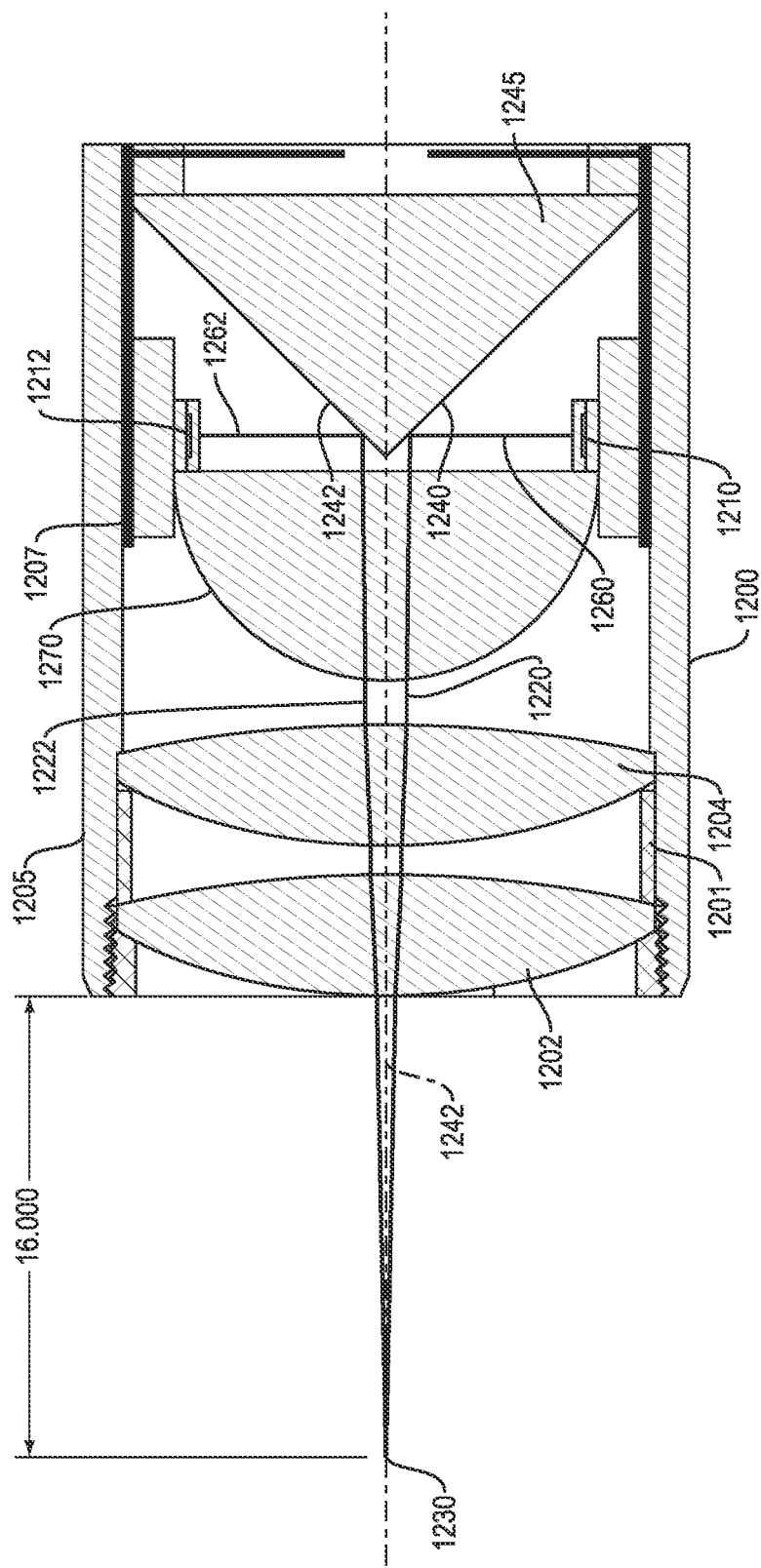
FIG. 12A illustrates a cross sectional view of a first aspect of a fifth exemplary embodiment of a lighting element in accordance with the principles of the invention.

FIG. 12A illustrates a cross sectional view of a first aspect of a fifth exemplary embodiment of a lighting element in accordance with the principles of the invention.

In this first aspect of the fifth exemplary embodiment shown, lighting element 1200 comprises elements similar to those described with regard to FIG. 10A, and a full understand of these elements may be obtained from the description provided in FIG. 10A.

For example, light generated by first lighting module 1210 is directed along light path 1260 and impinges upon reflective surface 1240. Reflective surface 1240 redirects the light along light path 1220 toward lens assembly 1201. Similarly, light generated by second lighting module 1212 is directed along light path 1262 and impinges upon reflective surface 1242. Reflective surface 1242 redirects the light along light path 1222 toward lens assembly 1201.

Further illustrated is lens 1270, similar to lens 1170, positioned substantially perpendicular to optical axis 1242. Lens 1270 is sized to capture light redirected from reflective surfaces 1240, 1242 and direct the captured light toward lens assembly 1201.

In this illustrated example, light generated by first lighting element 1210 and second lighting element 1222 is reflected by light director 1215, as previously described, to converge on to focal point 1230.

Figure 12B:
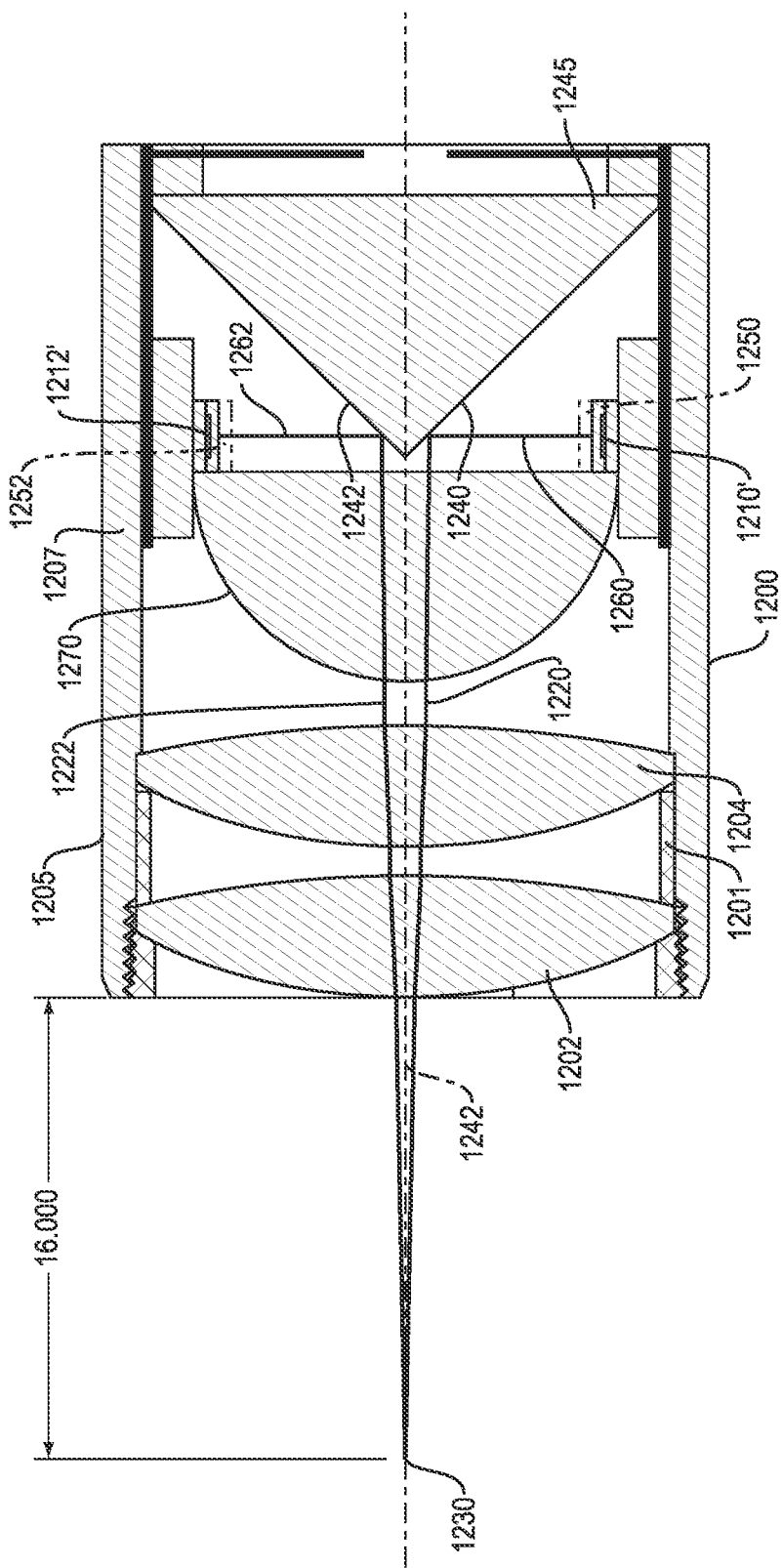
FIG. 12B illustrates a cross sectional view of a second aspect of a fourth exemplary embodiment of a lighting element in accordance with the principles of the invention.

FIG. 12B illustrates a cross sectional view of a second aspect of the exemplary embodiment of the lighting element shown in FIG. 12A.

This second aspect of lighting elements 940, 945 is comparable to the first exemplary embodiment of lighting elements 940, 945 shown in FIG. 12A and, thus, detailed discussion of comparable elements is believed not necessary for the understanding of the principles of the invention claimed.

FIG. 12B further illustrates filter 1252 associated with lighting element 1212' and filter 1250 associated with lighting element 1210', wherein filters 1250 and 1252 are comparable to at least one of filter 412 and 416, which limit the light transmitted by first lighting element 1210' and 1212' to a known wavelength (e.g., first light or second light).

For example, filter 1250 may operate as filter 412 to filter the light generated by lighting element 1210' in a manner such that first light may be reflected off of, and redirected by, reflective surface 1240. Similarly, filter 1252 may operate as filter 416 to filter the light generated by lighting element 1212' in a manner such that a second light may be reflected off of, and redirected by, reflective surface 1242.

Although lens 1170, 1270 shown in FIGS. 11A, 11B, 12A and 12B are depicted as extending to the width of optical assembly 1107, 1207, it would be understood that lens 1170, 1270 may be included within a holder that extends to the width of optical assembly 1107, 1207, wherein the holder retains lens 1170, 1270 in place while lens 1170, 1270 may be sized to be sufficient to capture the light redirected by light director 1115, 1215, respectively.

Although, the redirected light is illustrated as being substantially parallel to optical axis 1042, 1142 and 1242 shown in FIGS. 10A-12B, it would be recognized that either the direction of the light impinging on light director 1015, 1115, 1215 or the angle of the sides of light director 1015, 1115, 1215 may be selected such that the redirected light may contact lens 1004, 1104, 1204 at an angle that is not substantially parallel to optic axis 1042, 1142, 1242. That is, with regard to FIG. 10A, for example, light paths 1020 and 1022 need not be substantially parallel to optical axis 1042 and, thus, do not contact lens 1004 substantially perpendicular to lens 1004.

Accordingly, the orientation of lighting sources 1010, 1012 or the orientation of the angle of light director 1015 may be altered such that redirected light may contact lens 1004 in a manner to consider the optical path through lens 1002, 1004 such that light is directed toward focal point 1030.

In accordance with one aspect of the invention shown in FIGS. 10A-12B, light assembly 940 may be configured to output or emit a white light, whereas light assembly 945 may output one or both of a first light and a second light.

In accordance with a second aspect of the invention, light assembly 940 may be configured to emit one of a white light and a first light and light assembly 945 may be configured to emit one of a white light and a second light.

As previously disclosed, the intensity of the light generated at second light may be significantly less that the intensity of the light generated at first light.

In one aspect of the invention, voltage applied to second lighting source (e.g., 1012', FIG. 10B) may be less than the voltage applied to the first lighting source (e.g., 1010', FIG. 10B), such that the light output of the second lighting source is less than the light output of the first lighting source.

In another aspect of the invention, a number of first lighting sources may be greater than a number of second light lighting sources. In this case, the greater number of first lighting sources generate a light output greater than the lesser number of second lighting sources to render the intensity of the first light greater than that of the second light at the known distance.

In still another embodiment of the invention, each of lighting elements 940 and 945 may comprise at least one a white light lighting source (e.g., 114a), at least one of a first light lighting source (e.g., 112a) and at least one of a second light lighting source (e.g., 116a), about an inner circumference of optical assembly 1007.

For example, utilizing a 4 sided pyramid light director 1015, two lighting sources 1010, 1012 may be positioned such that light generated by lighting sources 1010, 1012 are directed to opposing sides of light director 1015, while light source 1010' and light source 1012' may be positioned such that light generated by lighting sources 1010', 1012' may be directed to the remaining opposed sides of light director 1015 to direct light to the other sides of light director 1015.

In this embodiment each of lighting elements 940 and 945 may be used to generate one or more of the wavelengths disclosed herein.

Control of the output of light from one of the white light lighting sources or the color light lighting sources, may be implemented using a contact or contact-less switching mechanism.

For example, FIG. 5A illustrates a printed circuit board 505, on mounting plate 410, which includes electronic or electrical components that provide for a switching mechanism wherein at least one of the white light and the color lights may be emitted. A switch on printed circuit board 505, may be used direct electrical energy from a power source (i.e., 820 FIG. 8, 970 FIG. 9) to one of the white light lighting sources or the colored light lighting sources that may be housed within housing 110 (FIG. 1) or housing 925 (FIG. 9).

In one aspect of the invention, the remote switch control may comprise one of: a contact control or a contact-less control mechanism, which have been previously described. In accordance with the principles of the invention, after detection of a contact control signal or a contact-less control signal, an indication of the detection may be provided to a wireless communication system, which transmits the detected indication to the receiver on PCB 505.

PCB 505, in response to receiving the indication of a detection of a control signal, may alter a state of lighting elements 112, 114 and 116.

In accordance with another aspect of the invention, printed circuit board 505 may include at least a wireless communication receiving system that is responsive to a command from a remote switch control (not shown). For example, the wireless communication receiving system and the remote switch control may communicate using a BLUETOOTH communication protocol (or other well-known short range communication systems).

Although BLUETOOTH communication is disclosed, it would be understood that other forms of short-range wireless communication system (e.g., Zigbee, Z-Wave, 6LoWPAN, and other short range communication technologies) may be utilized without altering the scope of the invention.

In one aspect of the invention, a remote switch or switches may be a foot-pedal switch that may include one or more switches that a practitioner may operate using their foot. The use of a foot pedal switch is advantageous in a medical procedure, for example, where a practitioner may not be able to utilize their hands to change the light output (i.e., white light, colored light).

Figure 13:
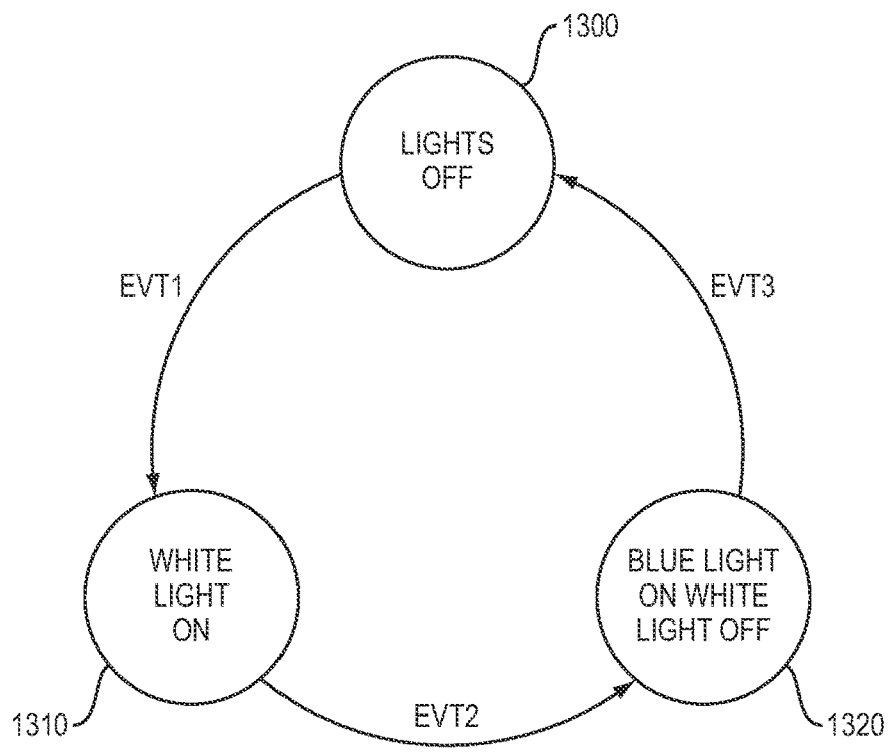
FIG. 13 illustrates an exemplary state diagram for processing associated with the control of a light assembly in accordance with the principles of the invention.

FIG. 13 illustrates a state diagram of an exemplary processing associated with the control of light assembly 110, for example, wherein a single contact control (e.g., a single foot pedal) is utilized.

In this exemplary state diagram, the light assembly 110 (or 925) is in an OFF-state wherein both white light and colored light lighting sources are in a "not-emitting" state. (state 1300).

In accordance with the principles of the invention, with the detection of a first event (EVT1) the white light lighting sources are "turned on" (state 1310).

As would be recognized, a first event (EVT1) and the other events discussed, herein, may be detected through one of a touch contact, a touchless-contact or a wireless contact.

Assuming a wireless contact where a remote switch includes a wireless connection to PCB 505, EVT1 may be indicated with a depression on the remote switch.

With the detection of a second depression of the remote switch, a second event (EVT2) is generated, wherein the white light lighting sources are "turned off" and the colored light lighting sources are "turned on" (state 1320). Finally, with the detection of a third event (EVT3), the processing returns to the initial state (state 1300) where all the lighting sources are turned off.

Figure 14:
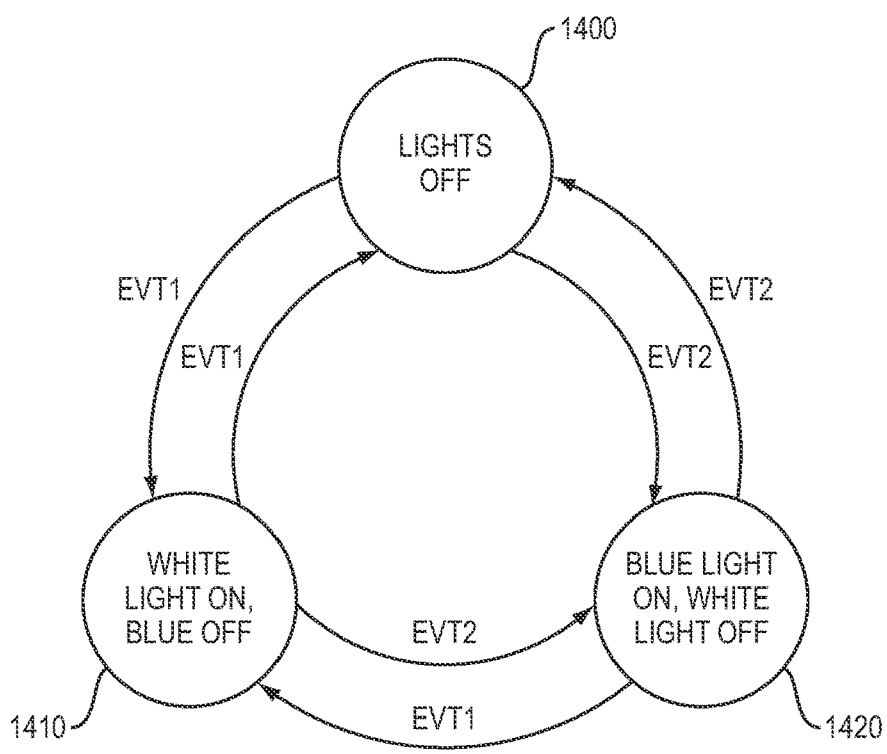
FIG. 14 illustrates a second exemplary state diagram for processing associated with the control of a light assembly in accordance with the principles of the invention.

FIG. 14 illustrates a state of a second exemplary processing associated with the control of light assembly 110 (925), wherein a double control (e.g., dual foot pedal) is utilized. In this exemplary processing, a left foot pedal of a remote switch may generate an EVT1 event whereas a right foot pedal may generate an EVT2 event.

In this exemplary state diagram, both white light lighting sources and colored light lighting sources are in an off (not-transmitting) state. (state 1400). With the detection of a first event (EVT1) (received through the wireless communication link) the white light lighting sources are "turned on" (state 1410).

With the detection of a next event, a determination is made whether the next event is one of a first event (EVT1) or a second event (EVT2). If the next event is determined to be a first event, processing proceeds to the initial state (state 1400) where the white light lighting sources are turned off.

However, if the next event is determined to be a second event (EVT2), then processing proceeds to state 1420 where the white light lighting sources are turned off and the colored light lighting sources are turned on.

In this state 1420 with the detection of a next event, a determination is made whether the next event is one of a first event (EVT1) or a second event (EVT2). If a first event (EVT1), processing returns to state 1410 to turn the white light lighting sources on and the colored light lighting sources off. However, if a second event (EVT2) is detected, the processing returns to the initial state 1400, wherein the white and colored lighting sources are turned off.

In summary a multi-light lamp assembly is disclosed that provides for the selected output of light using multiple light emitting sources, wherein the outputted light may be tailored to generate an expected response wavelength by the interaction of the emitted light and a tissue illuminated by the emitted light that allows a practitioner to distinguish between healthy and diseased tissues. Further disclosed is a viewing device, such as an eyewear, that includes a plurality of filters, which selectively prevent the ability to view the light transmitted by the light assembly while allowing a desired wavelength of light to be viewed.

In accordance with one aspect of the invention, lighting element 112 may emit a first light in a UV wavelength band, for example, whereas lighting element 116 may emit a second light in a blue wavelength band, for example. Lenses 644 may be formulated (whether absorptive or reflective) to filter wavelengths in the UV band while allowing wavelengths outside the UV band to be viewable. Accordingly, light generated by an object or tissue illuminated with the first light and/or the second light may be viewable while other wavelengths that may be harmful to the practitioner may be prevented from being viewed.

In accordance with another aspect of the invention, lighting element 112 may emit a first light in a lower range of the blue wavelength band, whereas lighting element 116 may emit a second light in an upper range of the blue light wavelength band. Lenses 644 may be formulated (whether absorptive or reflective) to filter wavelengths in associated with the lower range of the blue wavelength band while allowing wavelengths of the upper range of the blue light wavelength range to be viewable. Accordingly, light generated by an object or tissue illuminated with the first light and/or the second light may be viewable while other wavelengths that may be harmful to the practitioner may be prevented from being viewed.

Although specific configurations of a user-wearable visualization system have been discussed, it would be understood that other combinations of emitted light and filtered response may be incorporated into the visualization system disclosed and the examples provided, herein. The disclosed embodiments are not the only configuration considered and contemplated by the inventors.

Although the invention disclosed herein discusses specific wavelengths that are produced with currently available LEDs (i.e., non-lasing light emitting diodes and laser diodes), it would be recognized that the specific wavelengths absorbed and/or reflected may be changed and/or added to without altering the scope of the invention. In addition, it would be known in the art that the specific wavelengths discussed, herein, represent a band of wavelengths centered on the wavelength values presented herein to account for divergence of the wavelength generated by the LED during the generation of the light and/or the operation of the LED, wherein the light generated is represented as a nominal value.

The invention has been described with reference to specific embodiments. One of ordinary skill in the art, however, appreciates that various modifications and changes can be made without departing from the scope of the invention as set forth in the claims. Accordingly, the specification is to be regarded in an illustrative manner, rather than with a restrictive view, and all such modifications are intended to be included within the scope of the invention.

Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

The invention claimed is:

1. A user wearable device comprising:
   a light assembly, said light assembly comprising:
      a first light element configured to emit a first light at a first wavelength; and
      a second light element configured to concurrently emit a second light at a second wavelength, wherein the first wavelength and said second wavelength are positioned at different end points of a same wavelength band;
   an eyewear, said eyewear configured to:
      view a reflected light, wherein said reflected light comprises:
         a reflection of said emitted first light and said emitted second light and a light generated by an interaction of said emitted first light and emitted said second light with an object, said eyewear comprising:
         a first lens; and
         a second lens, each of said first lens and said second lens comprising:
            a filtering system, wherein said filtering system is configured to:
               attenuate said reflected light below a known wavelength value, wherein said known wavelength is between said emitted first wavelength and said second wavelength; and
               allow passage of light wavelengths of said reflected light above said known wavelength value.

2. The user wearable device as recited in claim 1, wherein each of said first lens and said second lens comprises:
   a magnification device, said magnification device configured to:
      magnify said second light by a known level of magnification, said magnification device comprising:
         at least one filter associated with said magnification device, said at least one filter associated with said magnification device configured to:
            attenuate said light wavelengths within said second light below said known wavelength value; and
            allow passage of said light wavelengths within said second light above said known wavelength value.

3. The user wearable device as recited in claim 1, wherein said first light element and said second light element are arranged about a central axis extending from said light assembly, wherein said first light and said second light are emitted toward a common point along said central axis.

4. The user wearable device as recited in claim 1, wherein first light element comprises:
   a first transmission filter, said first transmission filter configured to limit a wavelength range of said first light.

5. The user wearable device as recited in claim 4, wherein said first transmission filter is one of: a low pass filter and a bandpass filter.

6. The user wearable device as recited in claim 5, wherein an upper bound of said first transmission filter is selected to remove wavelengths from said first light having an intensity less than a maximum intensity of said second light.

7. The user wearable device as recited in claim 1, comprising:
   a third light element, said third light element configured to emit a white light, wherein said first light element, said second light element and said third light element are arranged concentrically about a central axis, wherein said first light element, said second light element and said third light element are arranged to project said first light, said second light and said third light toward a common point.

8. The user wearable device as recited in claim 1 wherein said first light is emitted in a lower range of a blue light wavelength range and said second light is emitted in an upper range of said blue light wavelength range.

9. The user wearable device as recited in claim 1, wherein said light assembly is removably attachable to said eyewear.

10. The user wearable device as recited in claim 1, comprising:
    one of: a headstrap and a headband, wherein said light assembly is removably attachable to said one of: a headstrap and a headband.

11. The user wearable device as recited in claim 1, wherein said second light element comprises:
    a second transmission filter, said second transmission filter configured to limit a wavelength range of said second light.

12. The user wearable device as recited in claim 1, wherein an intensity of said first light is greater than an intensity of said second light.

13. A user wearable device comprising:
    an eyewear positioned on a user, said eyewear comprising:
       a first lens; and
       a second lens, each of said first lens and said second lens comprising:
          a filtering system; and
    a light assembly attached to a headband positioned on said user, said light assembly comprising:
       a plurality of lighting elements arranged concentrically about a central axis extending from said light assembly and oriented to project a light generated by a corresponding one of said lighting elements to an object positioned along said central axis, wherein selected one of said plurality of lighting elements comprise:
a transmission filter, said transmission filter configured to limit a light wavelength range of said light projected by a corresponding one of said lighting elements, wherein said filter system is configured to:
attenuate light wavelengths within a second light below a known wavelength value, said second light comprising a reflection of said projected light and a fluorescent light generated by said object in response to being illuminated by said projected light; and
allow passage of light wavelengths within said second light above said known wavelength value, wherein said known wavelength is determined to allow on a portion of said projected light to pass.

14. The user wearable device as recited in claim 13, wherein selected ones of said plurality of lights project light concurrently.

15. The user wearable device as recited in claim 14, wherein said selected ones of said projected light is transmitted at different power levels.

16. The user wearable device as recited in claim 13, comprising:
a source of electrical energy, said source configured to generate a voltage; and
an electrical circuitry comprising:
a switch control configured to:
generate an indication of a change in state of a remote switch; and
a switch, said switch configured to:
receive said indication of said change in state of said remote switch; and
control, in response to said received indication, an application of said voltage to at least one of said plurality of lighting elements.

17. The user wearable device as recited in claim 16, wherein said remote switch is in communication with said electrical circuitry through a short-range communication protocol.

18. A user wearable device comprising:
an eyewear comprising:
a first lens; and
a second lens, each of said first lens and said second lens comprising:
a filter system; and
a light assembly, said light assembly comprising:
a plurality of lighting elements, each of said plurality of lighting elements comprising:
a lighting source configured to:
generate a substantially white light, wherein selected ones of said plurality of lighting elements comprise:
a transmission filter, said transmission filter configured to limit a light wavelength range of said light generated by a corresponding one of said light sources; and
an electronic circuitry comprising:
a receiving system configured to:
receive an indication of a change of state of a remote switch; and
control an application of a voltage to selected ones of said plurality of lighting elements to cause said selected ones of said plurality of lighting element to concurrently emit a light in respond to said received indication of said change of state, wherein said filter system is configured to:
attenuate light wavelengths within a second light below a known wavelength value, wherein said second light comprises wavelengths of said emitted light and a fluorescent light, and
allow passage of light wavelengths within said second light above said known wavelength value, wherein said known wavelength is determined to allow a portion of said emitted light to pass.

19. The user wearable device as recited in claim 18, wherein at least one of said at selected ones of said plurality of lighting elements emit said light in a lower range of a blue light wavelength range and a second one of said selected ones of said plurality of lighting elements emit said light in an upper range of said blue light wavelength range.

20. The user wearable device as recited in claim 18, wherein said concurrently emitted light is emitted at different power levels.

21. The user wearable device as recited in claim 18, wherein said known wavelength value is greater than said emitted light in said lower range of a blue light wavelength range; and
less than said emitted light in said upper range of said blue light wavelength range.

* * * * *